United States Patent
Splett et al.

(10) Patent No.: US 6,915,167 B2
(45) Date of Patent: Jul. 5, 2005

(54) METHOD AND APPARATUS FOR HARDWARE/FIRMWARE TRAP

(75) Inventors: Vincent E. Splett, Apple Valley, MN (US); Carl A. Schu, Plymouth, MN (US); Mark Haerle, Bloomington, MN (US); Paul J. Huelskamp, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 511 days.

(21) Appl. No.: 09/953,414

(22) Filed: Sep. 14, 2001

(65) Prior Publication Data

US 2002/0091417 A1 Jul. 11, 2002

Related U.S. Application Data

(63) Continuation-in-part of application No. 09/755,425, filed on Jan. 5, 2001, now Pat. No. 6,584,356.

(51) Int. Cl.⁷ .................................................. A61N 1/36
(52) U.S. Cl. ........................................................ 607/59
(58) Field of Search .............................. 607/30, 32, 59, 607/60; 128/903

(56) References Cited

U.S. PATENT DOCUMENTS

| 4,004,283 A | 1/1977 | Bennett et al. |
| 4,211,235 A | 7/1980 | Keller, Jr. et al. |
| 4,357,943 A | 11/1982 | Thompson et al. |
| 4,404,972 A * | 9/1983 | Gordon et al. ................ 607/16 |
| 4,476,868 A | 10/1984 | Thompson |
| 4,539,992 A | 9/1985 | Calfee et al. |
| 4,550,732 A | 11/1985 | Batty, Jr. et al. |
| 4,556,063 A | 12/1985 | Thompson et al. |
| 4,676,248 A | 6/1987 | Bernston |
| 4,726,024 A | 2/1988 | Guziak et al. |
| 4,751,589 A | 6/1988 | Kominami et al. |
| 5,052,388 A | 10/1991 | Sivula et al. |
| 5,127,404 A | 7/1992 | Wyborny et al. |
| 5,345,362 A | 9/1994 | Winkler |
| 6,412,081 B1 * | 6/2002 | Koscal et al. ................ 714/34 |

FOREIGN PATENT DOCUMENTS

| DE | 36 43 560 A1 | 7/1987 |
| DE | 10001042 | 7/2001 |
| EP | 0 947 920 A2 | 10/1999 |
| JP | 58186875 | 10/1983 |

* cited by examiner

Primary Examiner—Kennedy Schaetzle
Assistant Examiner—Kristen Mullen
(74) Attorney, Agent, or Firm—Michael C. Soldner; Girma Wolde-Michael

(57) ABSTRACT

A method and an apparatus for a hardware/firmware trap. At least one set of a firmware code is executed for operation of the device. Modification to the operation of the device is performed. The modification to the operation comprises: receiving a patch code; creating a firmware trap; generating an interrupt in response to the firmware trap; and executing the patch code in response to the interrupt.

8 Claims, 18 Drawing Sheets

METHOD AND APPARATUS FOR HARDWARE/FIRMWARE TRAP

CROSS REFERENCE TO RELATED APPLICATIONS

This application is a continuation-in-part of U.S. patent application Ser. No. 09/755,425 filed on Jan. 5, 2001, now U.S. Pat. No. 6,584,356.

FIELD OF THE INVENTION

This invention relates generally to implantable medical devices and, more particularly, to a hardware/firmware trap for efficiently modifying an operation of an implantable medical devices.

DESCRIPTION OF THE RELATED ART

Since the introduction of the first implantable pacemakers in the 1960s, there have been considerable advances in both the fields of electronics and medicine, such that there is presently a wide assortment of commercially available body-implantable electronic medical devices. The class of implantable medical devices now includes pacemakers, implantable cardioverters, defibrillators, neural stimulators, and drug administering devices, among others. Today's state-of-the-art implantable medical devices are vastly more sophisticated and complex than earlier ones. Today's state-of-the-art implantable medical devices are capable of performing significantly more complex tasks. The therapeutic benefits of such devices have been well proven.

As the functional sophistication and complexity of implantable medical device systems have increased over the years, it has become increasingly useful to include a system for facilitating communication between one implanted device and another implanted or external device, for example, a programming console, monitoring system, or the like. Shortly after the introduction of the earliest pacemakers, it became apparent that it would be desirable for physicians to non-invasively obtain information regarding the operational status of the implanted device, and/or to exercise at least some control over the device, e.g., to turn the device on or off or adjust the pacing rate, after implant. As new, more advanced features have been incorporated into implantable devices, it has been increasingly useful to convey correspondingly more information to/from the device relating to the selection and control of those features.

In particular, implantable pacemaker therapies have grown in number and complexity. In conventional devices this growth in the number and complexity of the various implantable pacemaker therapies has led to numerous feature interactions. These feature-to-feature interactions may adversely affect the efficacy of various of the implantable pacemaker therapies. Additionally, conventional devices have provided support for downloadable software, also known as random access memory-ware (RAMware), but the RAMware designs for conventional devices typically are uniform, documented in the product specification, firmware functional design and code listings, "set in stone" as it were. Consequently, the RAMware designs for conventional devices typically are difficult to design and/or implement and are relatively inflexible and expensive to reprogram, change and/or improve. For example, a set of "patch points" are provided, a fixed number of points in the code where "patch" code could be checked for and, if present, executed.

These patch points typically are not in locations best suited for a particular RAMware application, resulting in a limitation of the functionality of the RAMware application. This limitation of the functionality of the RAMware application has typically made RAMware impractical for many complex features, restricting the use of RAMware to primarily short-term research tools. This limitation of the functionality of the RAMware application could also inflate the size of a patch, since large block of code that had been bypassed often needed to be replicated to achieve the desired functionality. Since the RAMware applications have to reside among the existing "tasks" in the embedded firmware, the RAMware applications could also create timing problems, making it difficult for the firmware to achieve all of the firmware deadlines. Additionally, there is typically no way to preserve and/or back up a RAMware application through a device reset.

Many times it may be desirable to modify the normal operation of the implanted medical device. However, interrupting the normal flow of operations of the medical device can cause the device to become unstable. For example, executing the number of correction codes in RAM memory may cause errors in the operation of the implanted medical device, due to data loss in the RAM memory. Furthermore, data in RAM memory may be lost due to resets, or other electronic events. Therefore, using current methodologies, it is difficult and inefficient to perform patchwork corrections, modifications, and/or upgrades to the operation of the implanted medical device.

The present invention is directed to overcoming, or at least reducing the effects of, one or more of the problems set forth above.

SUMMARY OF THE INVENTION

In one aspect of the present invention, a method is provided for performing a hardware/firmware trap. At least one set of a firmware code is executed for operation of the device. Modification to the operation of the device is performed. The modification to the operation comprises: receiving a patch code; creating a firmware trap; generating an interrupt in response to the firmware trap; and executing the patch code in response to the interrupt.

In another aspect of the present invention, an apparatus is provided for a hardware/firmware trap. The apparatus of the present invention comprises: a controller for executing at least one set of a firmware code; and a hardware/firmware trap unit operatively coupled with the controller, the hardware/firmware trap to provide a firmware trap for interrupting normal execution of the firmware code and executing a patch code in response to the hardware/firmware trap.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which:

FIG. 1 schematically illustrates an implantable medical device (IMD) system according to the present invention;

FIG. 2 schematically illustrates a general block diagram of electronic circuitry for the implantable medical device (IMD) system of FIG. 1;

FIG. 3 schematically illustrates a perspective view of one embodiment of the programming unit for the implantable medical device (IMD) system of FIG. 1;

FIG. 4 schematically illustrates a general block diagram of various illustrative embodiments of a method and a device according the present invention comprising an implantable medical device (IMD) and an implantable medical device (IMD) controller using a pre-emptive real-time operating system (RTOS), the controller having a firmware architecture allowing at least one of modular feature design, modular feature implementation, extensible feature design and extensible feature implementation;

FIG. 5 schematically illustrates an implantable medical device (IMD) controller having a plurality of modular features;

FIG. 6 schematically illustrates controlling an implantable medical device (IMD) using an implantable medical device (IMD) controller by adding a modular feature to lower level firmware;

FIG. 7 schematically illustrates controlling an implantable medical device (IMD) using an implantable medical device (IMD) controller by modifying a modular feature in lower level firmware;

FIG. 8 schematically illustrates controlling an implantable medical device (IMD) using an implantable medical device (IMD) controller by deleting a modular feature from lower level firmware;

FIG. 9 schematically illustrates an implantable medical device (IMD) controller using a pre-emptive real-time operating system (RTOS) having a scheduling mechanism, a downloadable software interface and a non-volatile memory;

FIG. 10 schematically illustrates an implantable medical device (IMD) controller using a pre-emptive real-time operating system (RTOS) having a scheduling mechanism with a priority inheritance protocol, a downloadable software interface and a non-volatile memory;

FIG. 11 schematically illustrates an implantable medical device (IMD) controller using a pre-emptive real-time operating system (RTOS) having a scheduling mechanism, a downloadable software interface with call tables and an electrically erasable programmable read-only memory (EEPROM) non-volatile memory;

FIG. 12 schematically illustrates an implantable medical device (IMD) controller using a pre-emptive real-time operating system (RTOS) having a scheduling mechanism with a priority inheritance protocol, a downloadable software interface with call tables and an electrically erasable programmable read-only memory (EEPROM) non-volatile memory;

FIG. 13 schematically illustrates a block diagram depiction of an implementation of a hardware/firmware trap, in accordance with one embodiment of the present invention is illustrated;

FIG. 14 schematically illustrates a block diagram depiction of interaction between the CPU of FIG. 2 and the hardware/firmware trap unit of FIG. 13, in accordance with one embodiment of the present invention is illustrated;

FIG. 15 schematically illustrates a block diagram depiction of one embodiment of the trapping unit of FIG. 14, in accordance with one embodiment of the present invention is illustrated;

FIG. 16 schematically illustrates a flowchart depiction of the method of implementing a hardware/firmware trap, in accordance with one embodiment of the present invention;

FIG. 17 schematically illustrates a flowchart depiction of the method of determining a modification to the execution of the firmware code of the implanted medical device using a hardware/firmware trap, as indicated in FIG. 16, in accordance with one embodiment of the present invention; and FIG. 18 schematically illustrates a flowchart depiction of the method of setting-up a hardware/firmware trap, as indicated in FIG. 16, in accordance with one embodiment of the present invention.

Figure 1:
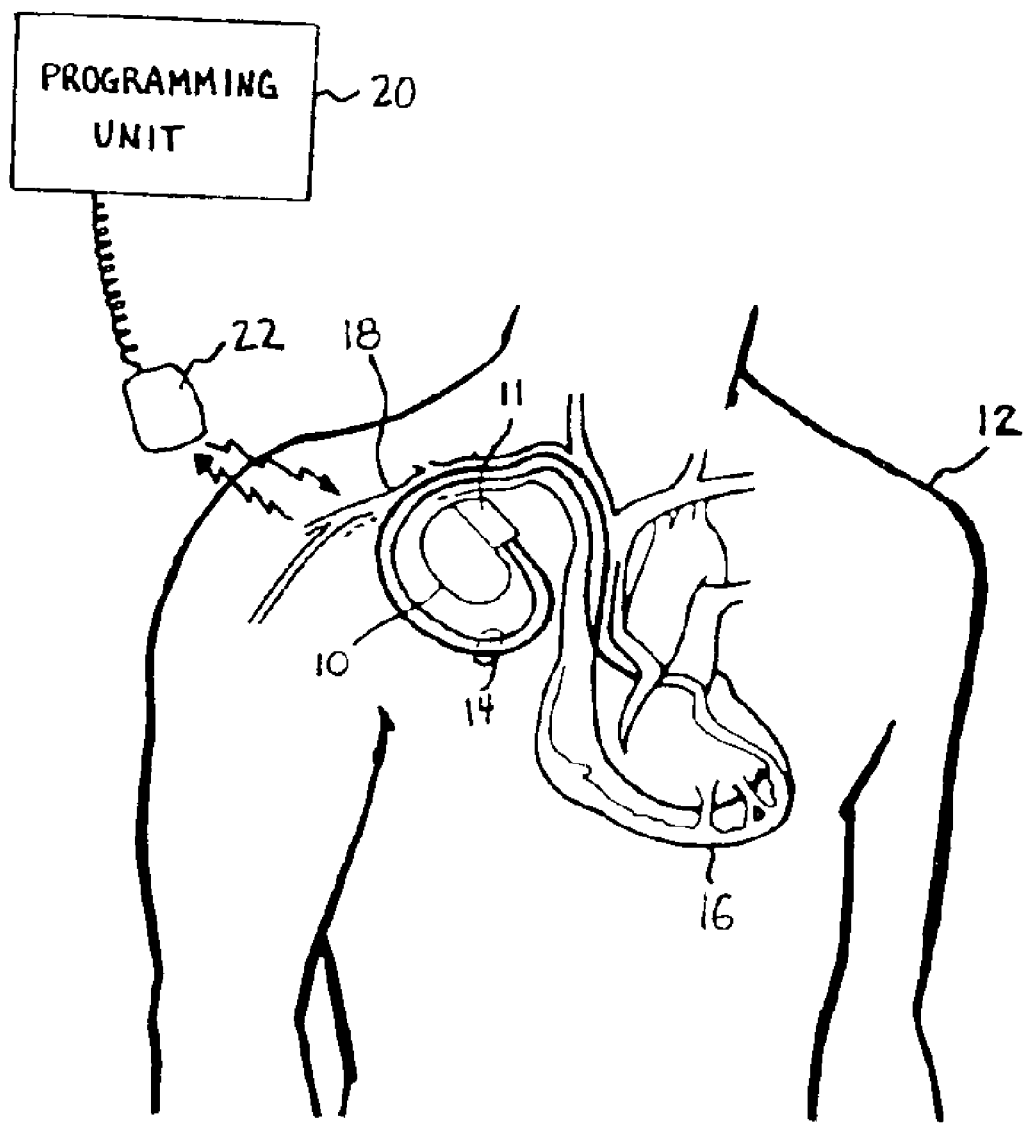
FIGS. 1–18 schematically illustrate various embodiments of a method and a device according to the present invention; and, more particularly.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of an apparatus and a method for operation of the apparatus according to the present invention are shown in FIGS. 1–12. FIG. 1 illustrates an implantable medical device (IMD) system 108, which includes, for example, an implantable pacemaker 110 that has been implanted in a patient 112. The pacemaker 110 is housed within a hermetically sealed, biologically inert outer canister or housing 113, which may itself be conductive so as to serve as an electrode in the pacemaker's pacing/sensing circuit. One or more pacemaker leads, collectively identified with reference numeral 114 in FIG. 1 are electrically coupled to the pacemaker 110 in a conventional manner and extend into the patient's heart 116 via a vein 118. Disposed generally near a distal end of the leads 114 are one or more exposed conductive electrodes for receiving electrical cardiac signals or delivering electrical pacing stimuli to the heart 116. The leads 114 may be implanted with their distal end situated in either the atrium or ventricle of the heart 116.

Although the present invention is described herein in an embodiment that includes a pacemaker, it may be advantageously embodied in numerous other types of implantable medical device systems in which it is desirable to provide a communication link between two physically separated components and retrieve data stored therein.

FIG. 1 also depicts an external programming unit 120 for non-invasive communication with the implanted device 110 via conventional uplink and downlink communication channels, which are not described in greater detail herein so as to avoid unnecessarily obscuring the instant invention. Associated with the programming unit 120 is a programming head 122, in accordance with conventional medical device programming systems, for facilitating two-way communication between the pacemaker 110 and the programmer 120. In many known implantable device systems, the programming head 122, such as that depicted in FIG. 1, is positioned on the patient's body over the implant site of the device 110 (usually within about 2 to about 3 inches, or equivalently, about 5 to about 8 cm, of skin contact), such that one or more antennas within the head 122 can send radio frequency (RF) signals to, and receive radio frequency (RF) signals from, an antenna (not shown) disposed within the hermetic enclosure of the implanted device 110 or disposed within a connector block 111 of the device 110, in accordance with common practice in the art.

Figure 2:
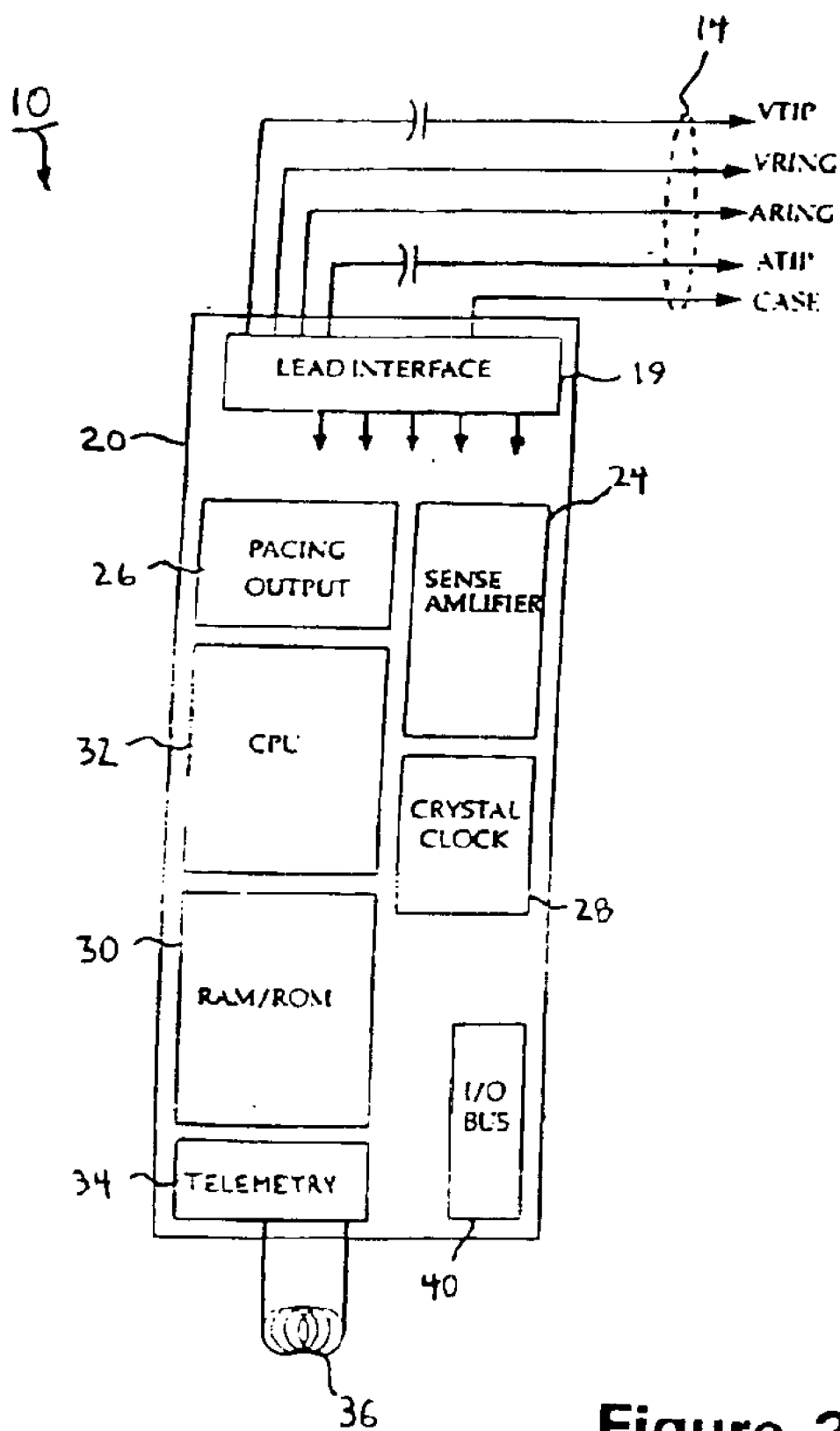

FIG. 2 provides a general block diagram of electronic circuitry that makes up the pacemaker 110. The pacemaker 110 is a device capable of performing a variety of functions, such as delivering electrical stimulation therapy to the patient 112 in accordance with the presently disclosed embodiment of the invention. FIG. 2 shows that pacemaker 110 comprises circuitry for controlling the device's pacing and sensing functions. Aspects of the pacemaker circuitry may be of conventional design, in accordance; for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the pacemaker 110 are conventional in their design and operation, such components will not be described herein in detail, as it is believed that design and implementation of such components would be a matter of routine practice to those of ordinary skill in the art. For example, the circuitry of the pacemaker 110 shown in FIG. 2 includes sense amplifier circuitry 224, stimulating pulse output circuitry 226, a crystal clock 228, a random-access memory and read-only memory (RAM/ROM) unit 230, and a pacing timing and control circuit in the form of a programmed central processing unit (CPU) 232, all of which are well-known in the art.

The pacemaker 110 also includes an internal telemetry communications circuit 234 coupled to an antenna 236 so that it is capable of communicating with the external programmer/control unit 120. Various telemetry systems for providing the uplink and downlink communication channels between the external programming unit 120 and the implanted pacemaker 110 have been shown in the art and may be employed herein without departing from the spirit and scope of the instant invention. Exemplary communication telemetry systems that may be utilized herein are disclosed, for example, in the following U.S. Patents: U.S. Pat. No. 4,539,992 to Calfee et al. entitled "Method and Apparatus for Communicating With Implanted Body Function Stimulator," U.S. Pat. No. 4,550,732 to Batty Jr. et al. entitled "System and Process for Enabling a Predefined Function Within An Implanted Device," U.S. Pat. No. 4,751,589 to Slocum et al. entitled "Biomedical Implant With High Speed, Low Power Two-Way Telemetry," U.S. Pat. No. 4,676,248 to Berntson entitled "Circuit for Controlling a Receiver in an Implanted Device," U.S. Pat. No. 5,127,404 to Wyborny et al. entitled "Telemetry Format for Implanted Medical Device," U.S. Pat. No. 4,211,235 to Keller, Jr. et al. entitled "Programmer for Implanted Device," the above-referenced Markowitz '382 patent and U.S. Pat. No. 4,556,063 to Thompson et al. entitled "Telemetry System for a Medical Device." The Wyborny et al. '404 patent and the Thompson et al. '063 patent are hereby incorporated by reference herein in their respective entireties.

With continued reference to FIG. 2, the pacemaker 110 is coupled to one or more leads 114 which, when implanted, extend transvenously between the implant site of the pacemaker 110 and the patient's heart 116, as previously noted with reference to FIG. 1. Physically, the connections between the leads 114 and the various internal components of the pacemaker 110 are facilitated by a conventional connector block assembly 111, shown in FIG. 1 but not shown in FIG. 2. Electrically, the coupling of the leads 114 and the internal electrical components of the pacemaker 110 may be facilitated by a lead interface circuit 219, which functions, in a multiplexer-like manner, to selectively and dynamically establish necessary connections between various conductors in the leads 114, including, for example, atrial tip and ring electrode conductors ATIP and ARING and ventricular tip and ring electrode conductors VTIP and VRING, and individual electrical components of the pacemaker 110, as would be familiar to those of ordinary skill in the art. For the sake of clarity, the specific connections between the leads 114 and the various components of the pacemaker 110 are not shown in FIG. 2, although it will be clear to those of ordinary skill in the art that, for example, the leads 114 will necessarily be coupled, either directly or indirectly, to sense amplifier circuitry 224 and stimulating pulse output circuitry 226, in accordance with common practice, such that cardiac electrical signals may be conveyed to the sense amplifier circuitry 224, and such that stimulating pulses may be delivered to cardiac tissue, via the leads 114.

It will be appreciated that the signals received over the leads 114 by the sense amplifier circuitry 224 may be collected and stored in the RAM/ROM unit 230 by the CPU 232 acting under control of software also stored in the RAM/ROM unit 230. Additional data, such as the timing of signals delivered by the stimulating pulse output circuitry 226 may also be stored in the RAM/ROM unit 230. This stored data may be later retrieved and delivered to the programming unit 120 via the telemetry communications circuit 234.

As previously noted, the circuitry of the pacemaker 110 includes the central processing unit (CPU) 232 which may be an off-the-shelf programmable microprocessor or microcontroller, but in the presently illustrated embodiment of the invention is a custom integrated circuit. Although specific connections between the CPU 232 and other components of the pacemaker circuitry are not shown in FIG. 2, it will be apparent to those of ordinary skill in the art that the CPU 232 functions to control the timed operation of the stimulating pulse output circuit 226 and the sense amplifier circuit 224 under control of a program of instructions stored in the RAM/ROM unit 230. The crystal clock 228 in the presently illustrated embodiment is a crystal controlled oscillator that provides a main timing clock signal. Again, the lines over which such clock signals are provided to the various components of the pacemaker 110 (e.g., the CPU 232) are omitted from FIG. 2 for the sake of clarity. It is believed that those of ordinary skill in the art will be familiar with such an operative arrangement.

It is to be understood that the various components of the pacemaker 110 depicted in FIG. 2 are powered by means of a battery (not shown), which is contained within the hermetic enclosure of the pacemaker 110, in accordance with common practice in the art. For the sake of clarity in the drawings, the battery and the connections between it and the other components of the pacemaker 110 are not shown.

Stimulating pulse output circuitry 226, which functions to generate cardiac stimuli under control of signals issued by the CPU 232, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the present invention.

The sense amplifier circuitry 224, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety. Generally, the sense amplifier circuitry 224 functions to receive electrical cardiac signals from the leads 114 and to process such signals to derive event signals reflecting the occurrence of specific cardiac electrical events, including atrial contractions (P-waves) and ventricular contractions (R-waves). These event-indicating signals are provided to the CPU 232 for use by the CPU 232 in controlling the synchronous stimulating operations of the pacemaker 110 in accordance with common practice in the art. In addition, these event-indicating signals, as discussed above, may be communicated, via the uplink communication channel, to the external programming unit 120 for storage and visual display to a physician or clinician.

Those of ordinary skill in the art will appreciate that the pacemaker 110 may include numerous other components and subsystems, for example, activity sensors and associated circuitry. The presence or absence of such additional components in the pacemaker 110, however, is not believed to be directly pertinent to the present invention, which relates generally to the firmware architecture of a portion of the RAM/ROM unit 230, permitting modular feature design for the pacemaker 110, and to the method of operation of this firmware architecture.

Figure 3:
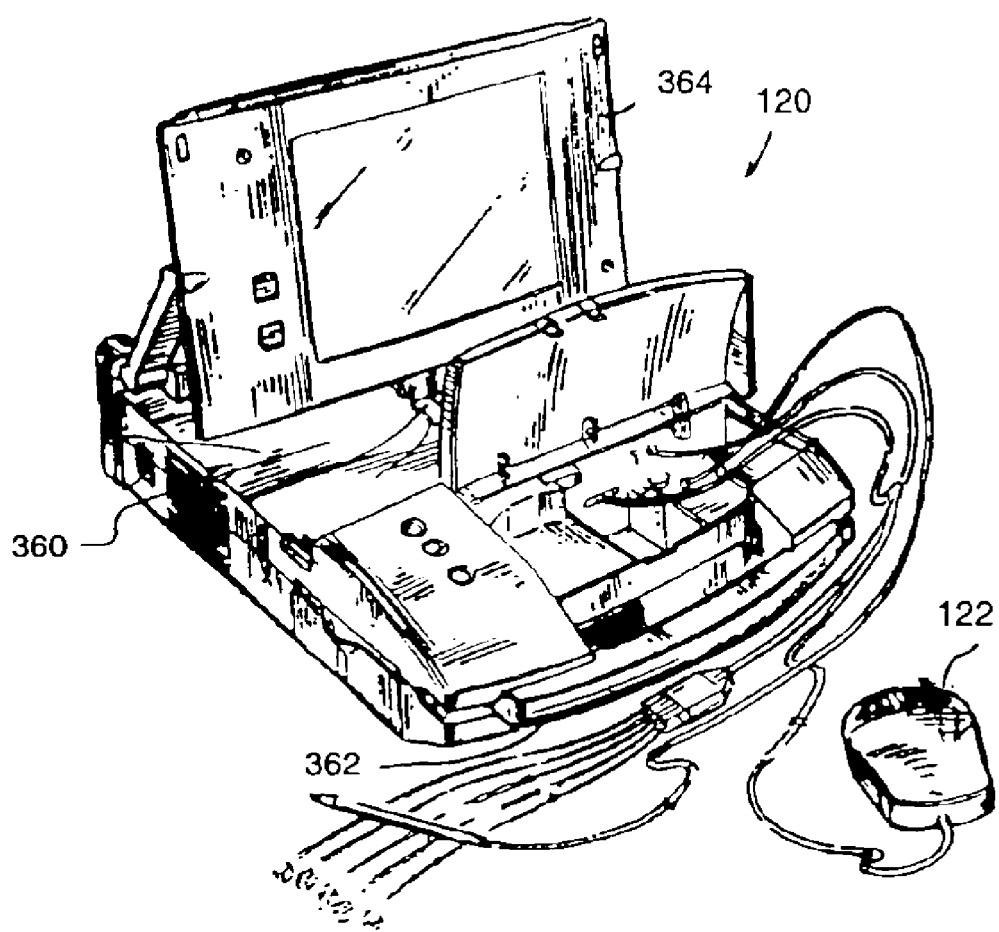

FIG. 3 shows a perspective view of one embodiment of the programming unit 120 in accordance with the presently disclosed embodiment of the invention. Internally, the programmer 120 includes a processing unit (not shown), which in accordance with the presently disclosed embodiment of the invention is a personal computer-type motherboard, for example, a computer motherboard including an Intel 80×86 microprocessor or the like and related circuitry such as digital memory.

Referring to FIG. 3, the programming unit 120 comprises an outer housing 360, which is preferably made of thermal plastic or another suitably rugged yet relatively lightweight material. A carrying handle, designated generally as 362 in FIG. 3, is integrally formed into the front of the housing 360. With the handle 362, the programming unit 120 can be carried like a briefcase.

An articulating display screen 364 is disposed on an upper surface of the housing 60. The display screen 364 folds down into a closed position (not shown) when the programming unit 120 is not in use, thereby reducing the size of the programming unit 120 and protecting the display surface of the display 364 during transportation and storage thereof.

A floppy disk drive is disposed within the housing 360 and is accessible via a disk insertion slot (not shown). A hard disk drive is also disposed within the housing 360, and it is contemplated that a hard disk drive activity indicator (e.g., an LED, not shown) could be provided to give a visible indication of hard disk activation.

As would be appreciated by those of ordinary skill in the art, it is often desirable to provide a means for the programming unit 120 to adapt its mode of operation depending upon the type of implanted device to be programmed. Accordingly, it may be desirable to have an expansion cartridge containing EPROMS or the like for storing program information to control the programming unit 120 to operate in a particular manner corresponding to a given type of implantable device.

In accordance with the presently illustrated embodiment of the invention, the programming unit 120 is equipped with an internal printer (not shown) so that a hard copy of a patient's electrocardiogram (ECG) or of graphics displayed on the programmer's display screen 364 can be generated. Several types of printers, such as the AR-100 printer available from General Scanning Co., are known and commercially available.

In the perspective view of FIG. 3, the programming unit 120 is shown with the articulating display screen 364 having been lifted up into one of a plurality of possible open positions such that the display area thereof is visible to a user situated in front of the programming unit 120. The articulating display screen 364 is preferably of the LCD or electro-luminescent type, characterized by being relatively thin as compared, for example, a cathode ray tube (CRT) or the like. The display screen 364 is operatively coupled to computer circuitry disposed within the housing 360, and is adapted to provide a visual display of graphics and/or data under control of the internal computer.

One embodiment of the programming unit 120 described herein with reference to FIG. 3 is described in more detail in U.S. Pat. No. 5,345,362 issued to Thomas J. Winkler, entitled "Portable Computer Apparatus With Articulating Display Panel," which patent is hereby incorporated herein by reference in its entirety. Also, the Medtronic Model 9760 or 9790 programmers are other implantable device programming units with which the present invention may be advantageously practiced.

Figure 4:
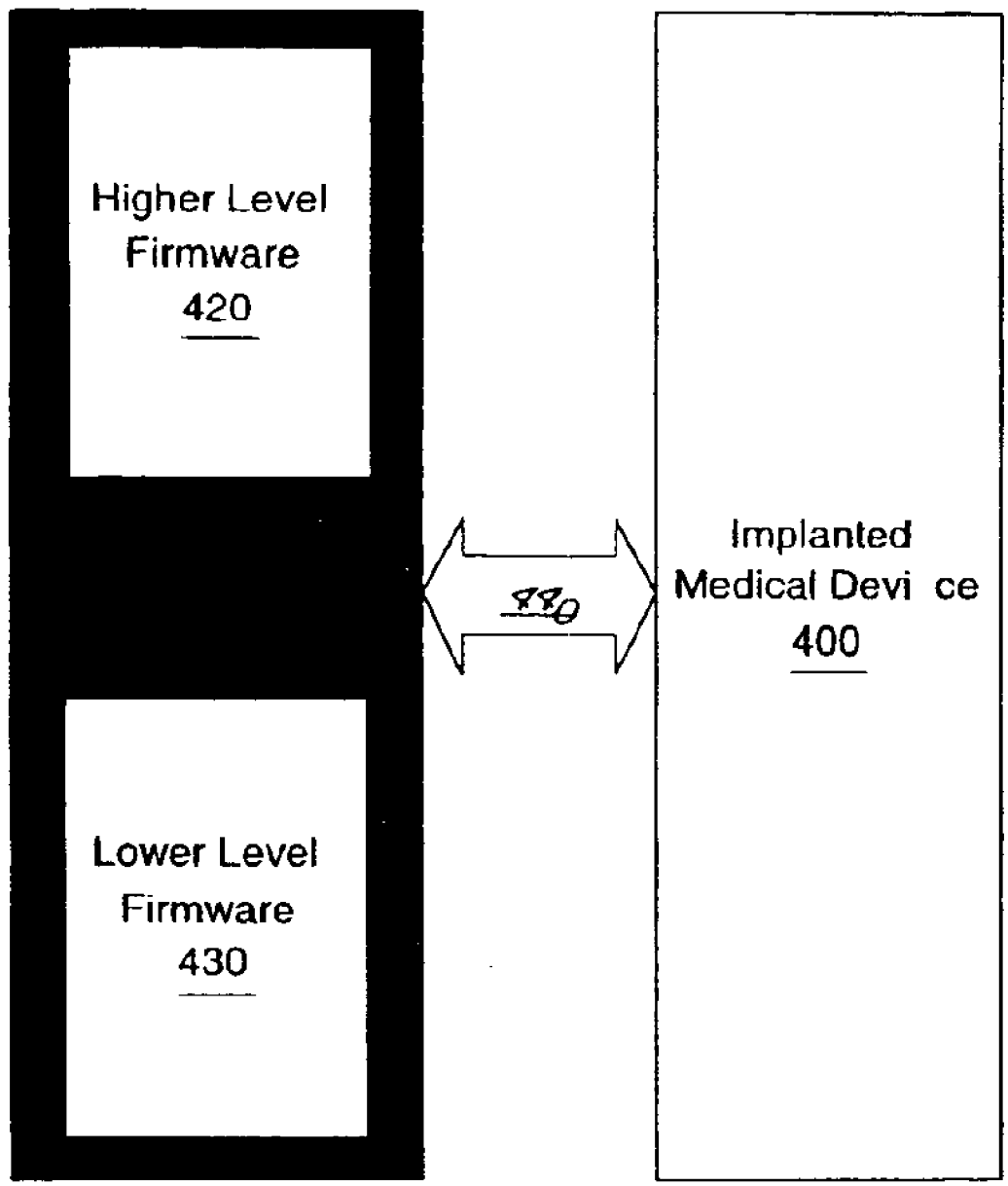

Turning to FIG. 4, a general block diagram of various illustrative embodiments of a device according the present invention is shown, comprising an implantable medical device (IMD) 400 and an implantable medical device (IMD) controller 410 controlling the implantable medical device 400. The implantable medical device (IMD) 400 may comprise an implantable pulse generator (IPG) for an implantable pacemaker, such as an implantable anti-brady pacemaker and/or an implantable anti-tachy pacemaker. The implantable medical device (IMD) controller 410 may have higher level firmware 420 and lower level firmware 430. The implantable medical device (IMD) 400 and the implantable medical device (IMD) controller 410 may communicate via coupler 440. The implantable medical device (IMD) controller 410 uses a pre-emptive real-time operating system (RTOS). The implantable medical device (IMD) controller 410 has a firmware architecture allowing at least one of modular feature design, modular feature implementation, extensible feature design and extensible feature implementation.

Figure 5:
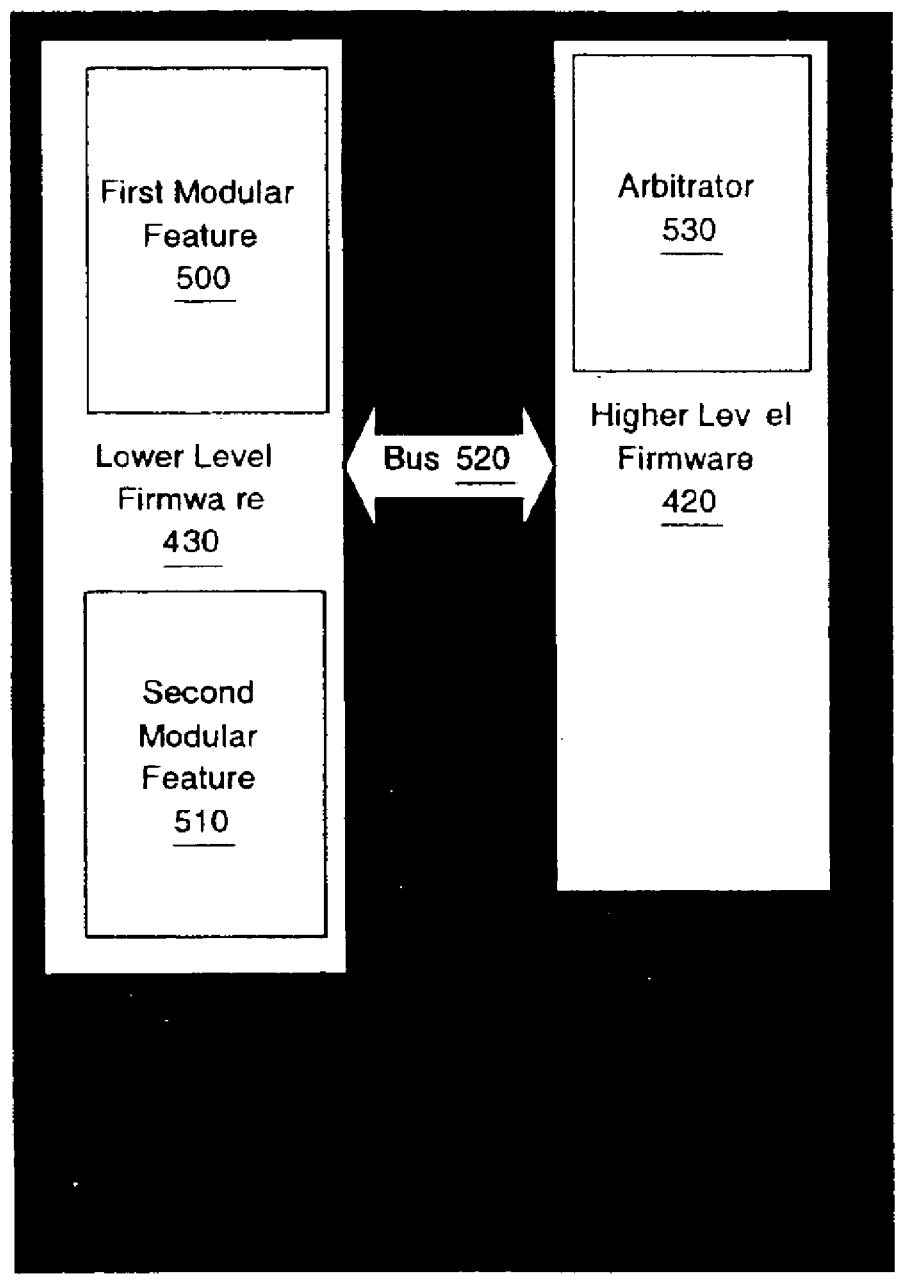

As shown in FIG. 5, the implantable medical device (IMD) controller 410 with the pre-emptive real-time operating system (RTOS) may have a plurality of modular features, such as first modular feature 500 and second modular feature 510. The firmware architecture of the implantable medical device (IMD) controller 410 may coordinate between and among the plurality of modular features, such as the first modular feature 500 and the second modular feature 510, to reduce feature-to-feature interactions.

The implantable medical device (IMD) controller 410 may also have a converter (not shown) enabling efficient conversion between at least one identifiable first modular feature, for example, the first modular feature 500, working in a rate domain (beats per minute or BPM), and at least one identifiable second modular feature, for example, the second modular feature 510, working in an interval domain (usually in milliseconds or msec). The converter may be included in the higher level firmware 420 and/or the lower level firmware 430. Alternatively, and/or additionally, the converter may be included elsewhere in the implantable medical device (IMD) controller 410. Some modular features output a desired pacing rate, and a higher level firmware "arbitrator" (such as firmware arbitrator 530 disposed in the higher level firmware 420, as shown in FIG. 5) may decide to use the desired pacing rate output by the modular feature or use another value from a different modular feature.

Figure 6:
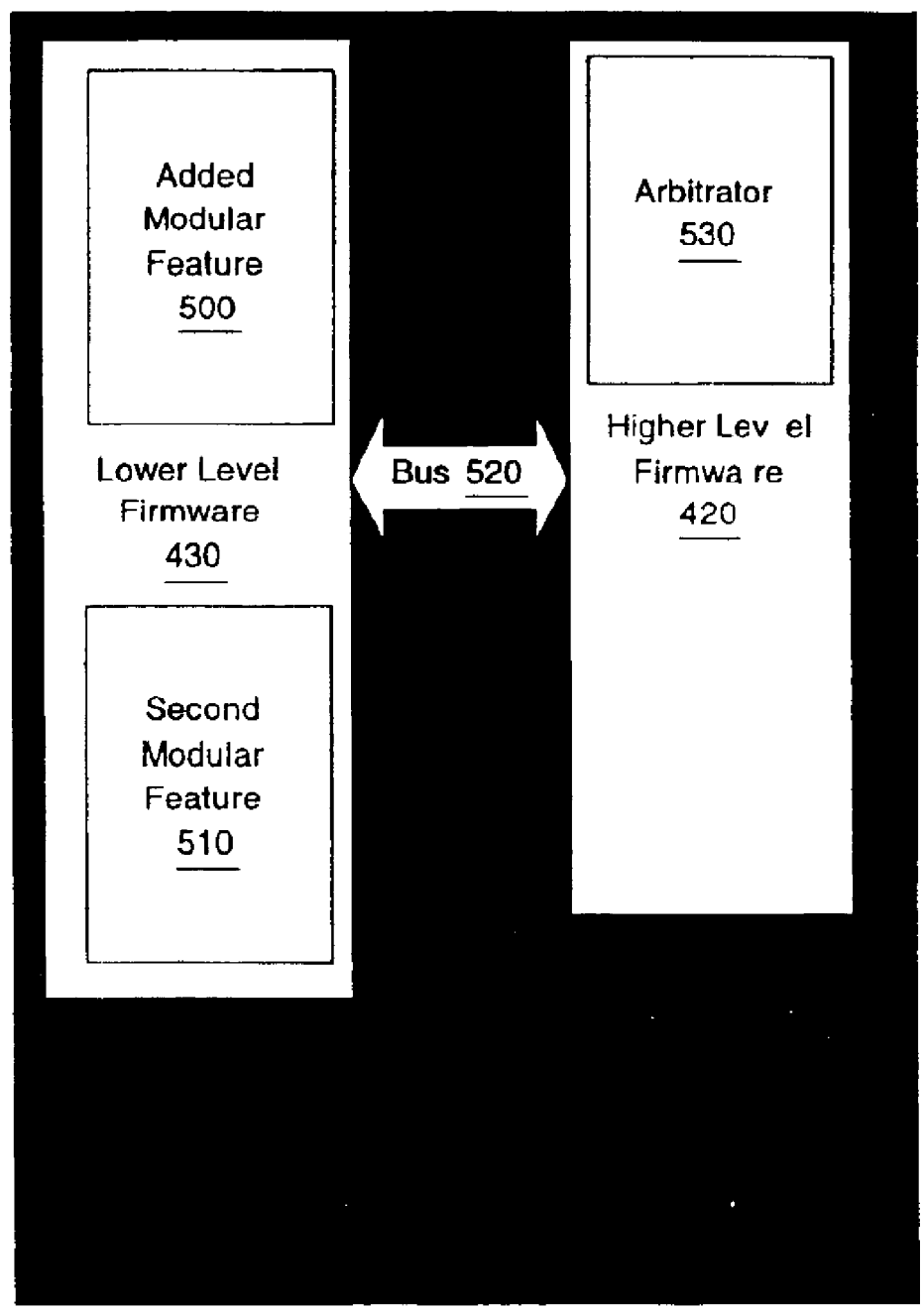
Figure 7:
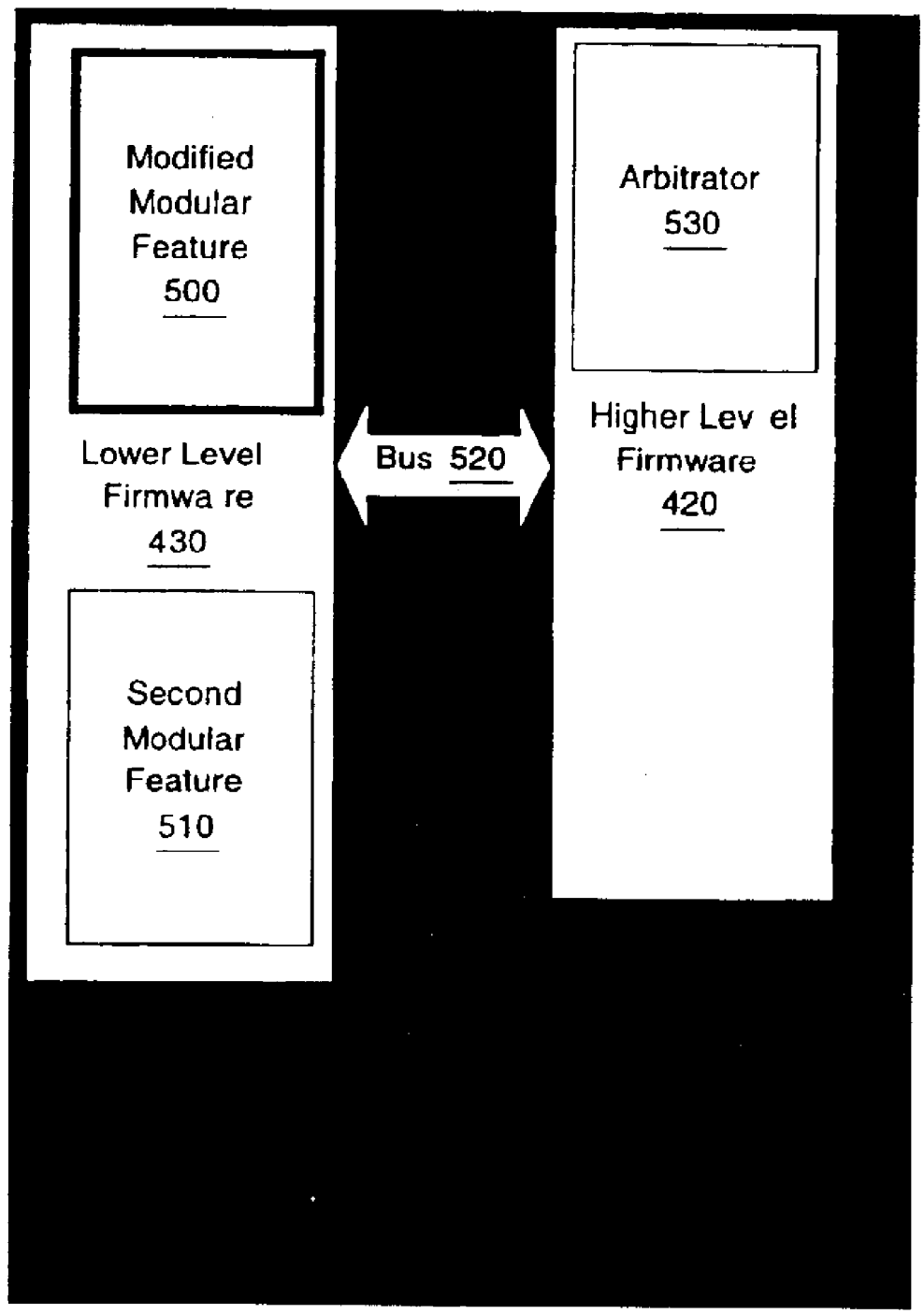
Figure 8:
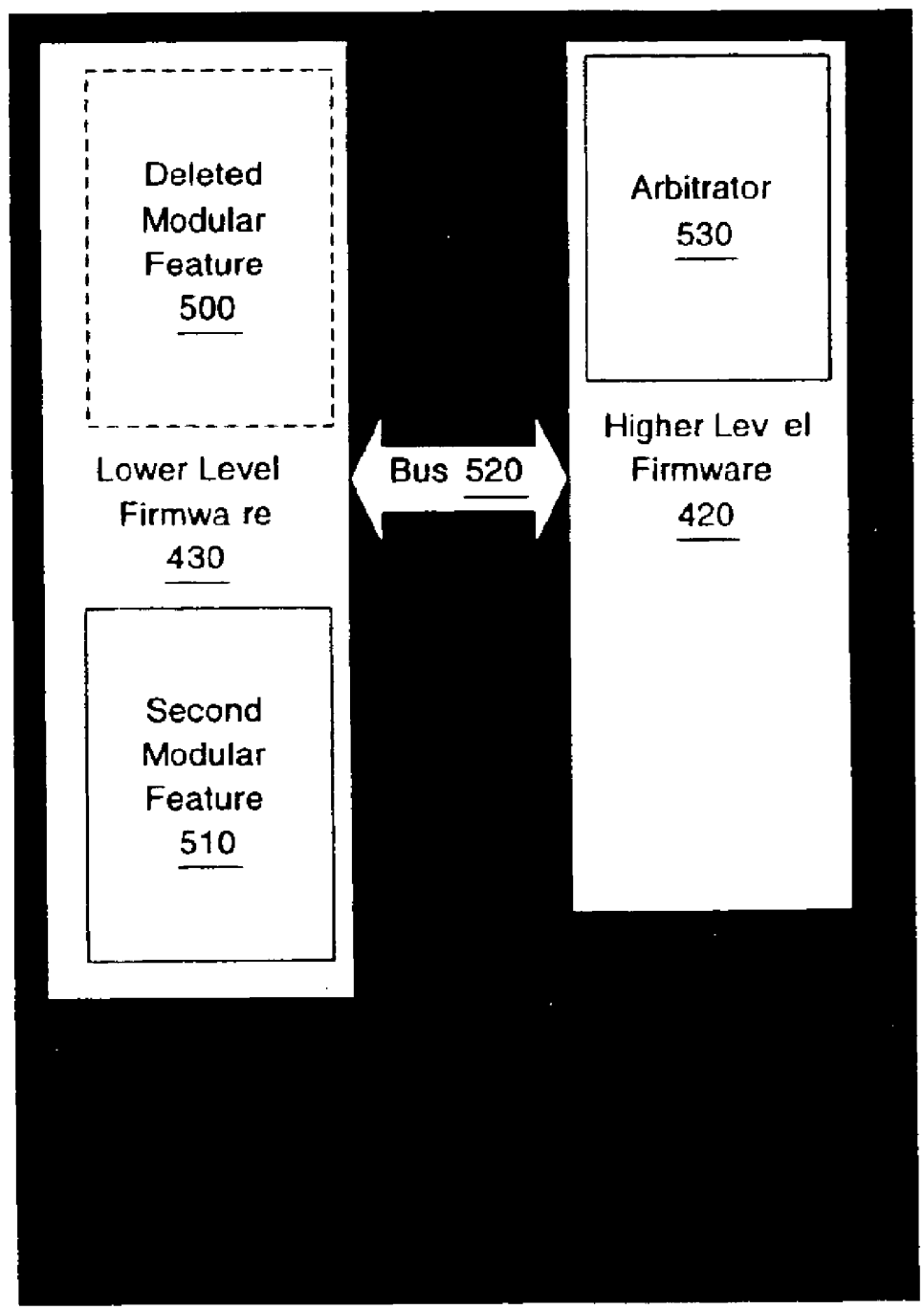

As shown in FIGS. 6–8, controlling the implantable medical device (IMD) 400 using the implantable medical device (IMD) controller 410 with the pre-emptive real-time operating system (RTOS) may comprise at least one of adding a modular feature to the firmware, modifying a modular feature of the firmware and deleting a modular feature from the firmware. As shown in FIG. 6, for example, controlling the implantable medical device (IMD) 400 using the implantable medical device (IMD) controller 410 may comprise adding a modular feature, such as added modular feature 600, to the lower level firmware 430. As shown in FIG. 7, for example, controlling the implantable medical device (IMD) 400 using the implantable medical device (IMD) controller 410 may comprise modifying a modular feature, such as modified modular feature 700, in the lower level firmware 430. As shown in FIG. 8, for example, controlling the implantable medical device (IMD) 400 using the implantable medical device (IMD) controller 410 may comprise deleting a modular feature, such as deleted modular feature 800 (shown in phantom), from the lower level firmware 430.

The implantable medical device (IMD) controller 410 firmware architecture, described in more detail below, allows at least one of modular feature design, modular feature implementation, extensible feature design and extensible feature implementation. In various illustrative embodiments, the firmware architecture itself, with the higher level firmware 420 communicating with and/or directing the lower level firmware 430 via bus 520, coordinates between and among the plurality of modular features, such as the first modular feature 500 and the second modular feature 510, to reduce feature-to-feature interactions. For example, the firmware architecture may coordinate between and among the first modular feature 500 and the second modular feature 510 to reduce feature-to-feature interactions by testing the first modular feature 500 and/or the second modular feature 510 to debug the first modular feature 500 and/or the second modular feature 510.

Figure 9:
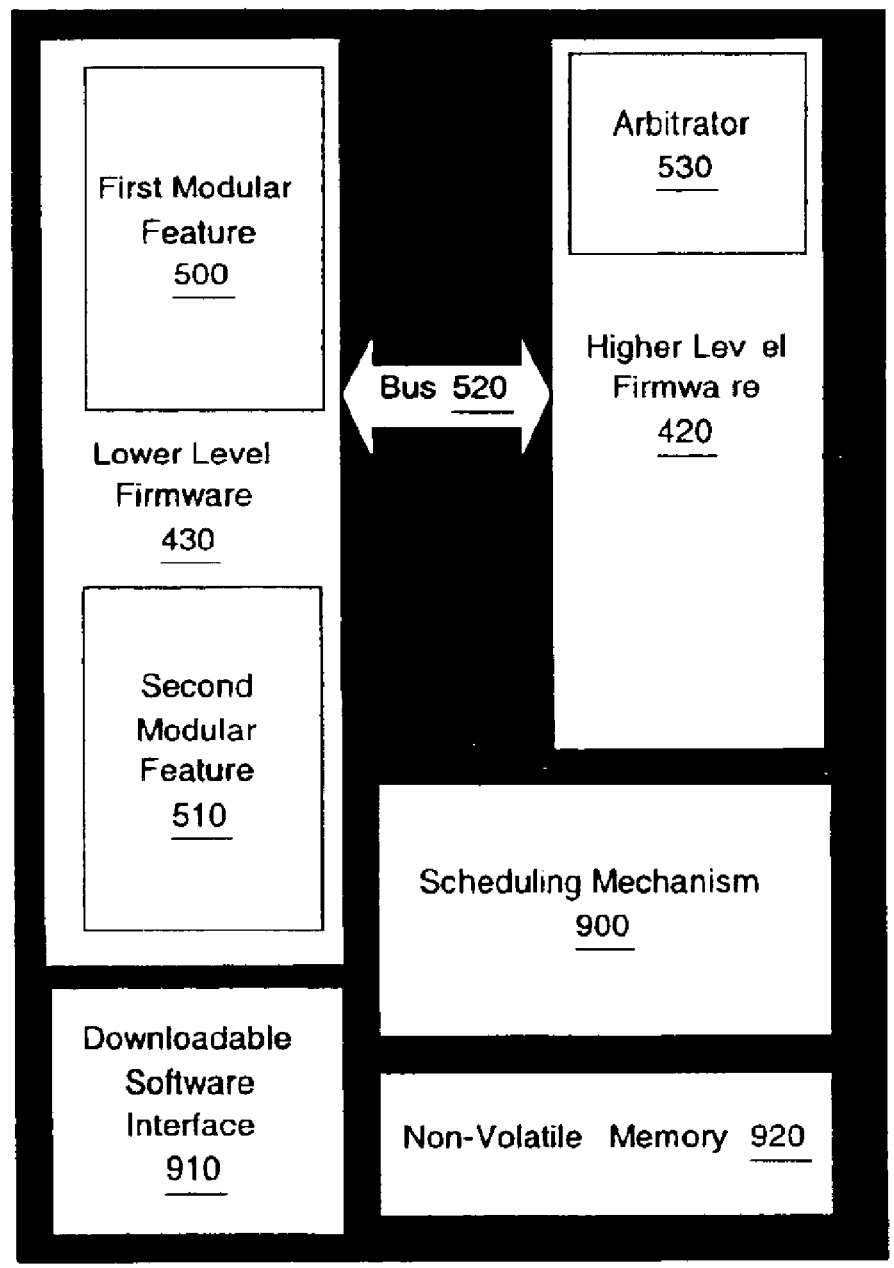

As shown in FIG. 9, the implantable medical device (IMD) controller 410 with the pre-emptive real-time operating system (RTOS) may have a scheduling mechanism 900. The implantable medical device (IMD) controller 410 may also have a downloadable software interface 910 and/or a non-volatile memory 920.

Figure 10:
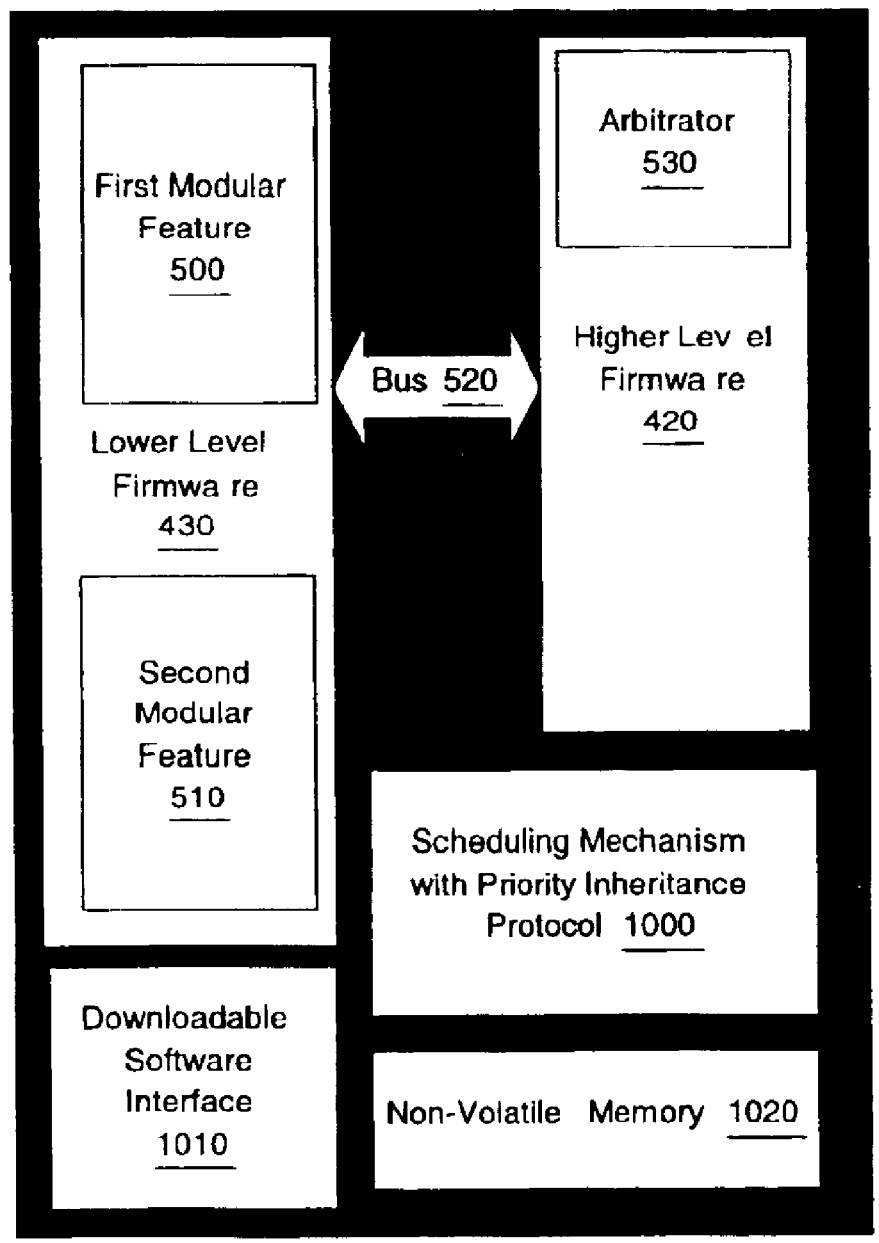

As shown in FIG. 10, the implantable medical device (IMD) controller 410 with the pre-emptive real-time operating system (RTOS) may have a scheduling mechanism 1000 with a priority inheritance protocol. The implantable medical device (IMD) controller 410 with the pre-emptive real-time operating system (RTOS) having the scheduling mechanism 1000 with the priority inheritance protocol may be capable of being analyzed using rate monotonic analysis. The implantable medical device (IMD) controller 410 with the pre-emptive real-time operating system (RTOS) having the scheduling mechanism 1000 with the priority inheritance protocol may be used in devices and/or systems that are resource-constrained, in terms of read-only memory (ROM), random access memory (RAM), power consumption, central processing unit (CPU) bandwidth, and the like. The implantable medical device (IMD) controller 410 with the pre-emptive real-time operating system (RTOS) having the scheduling mechanism 1000 with the priority inheritance protocol may also have a downloadable software interface 1010 and/or a non-volatile memory 1020.

Figure 11:
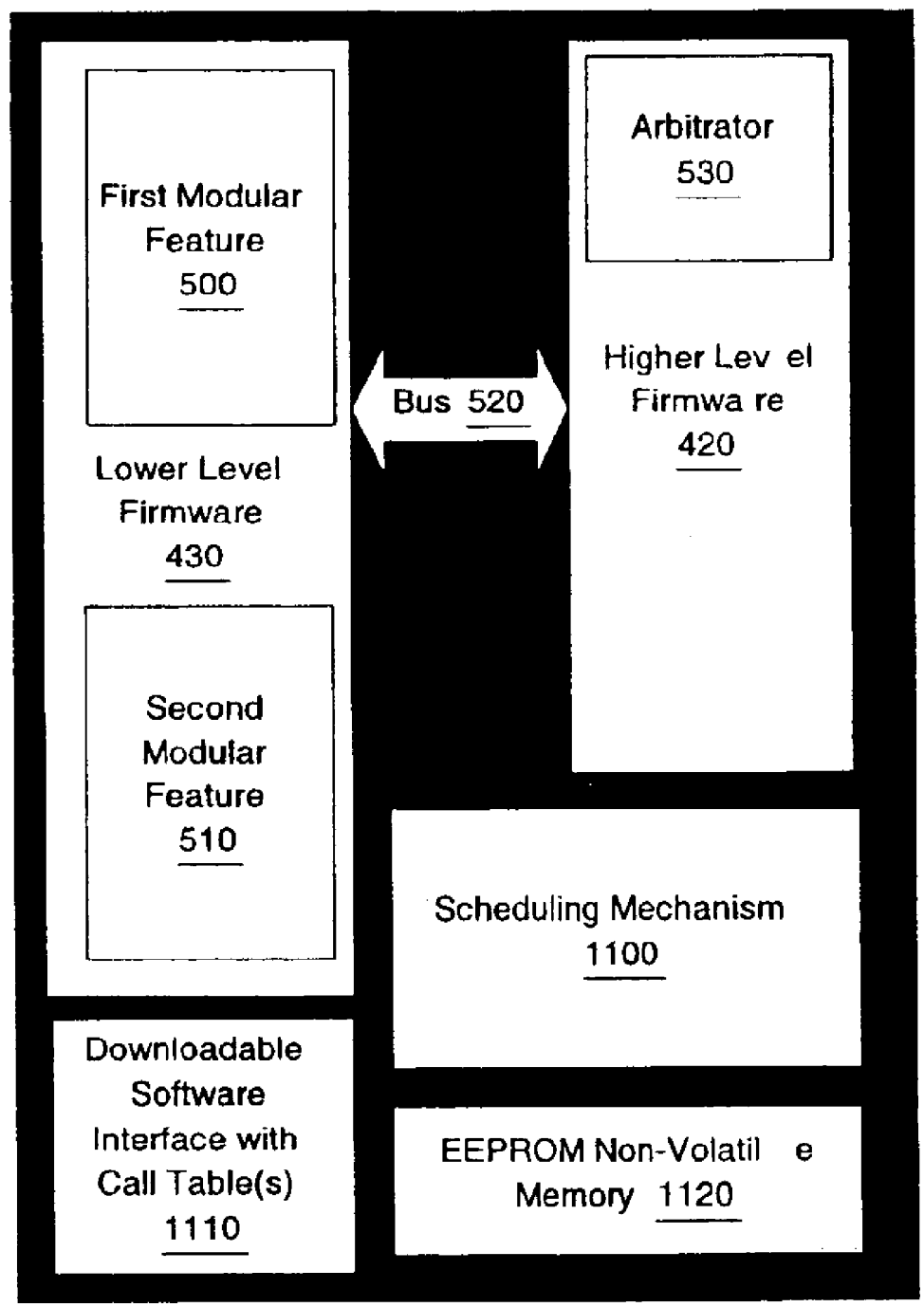

As shown in FIG. 11, the implantable medical device (IMD) controller 410 with the pre-emptive real-time operating system (RTOS) may have a scheduling mechanism 1100. The implantable medical device (IMD) controller 410 may also have a downloadable software interface 1110 with one or more call tables and/or an electrically erasable programmable read-only memory (EEPROM) non-volatile memory 1120.

Figure 12:
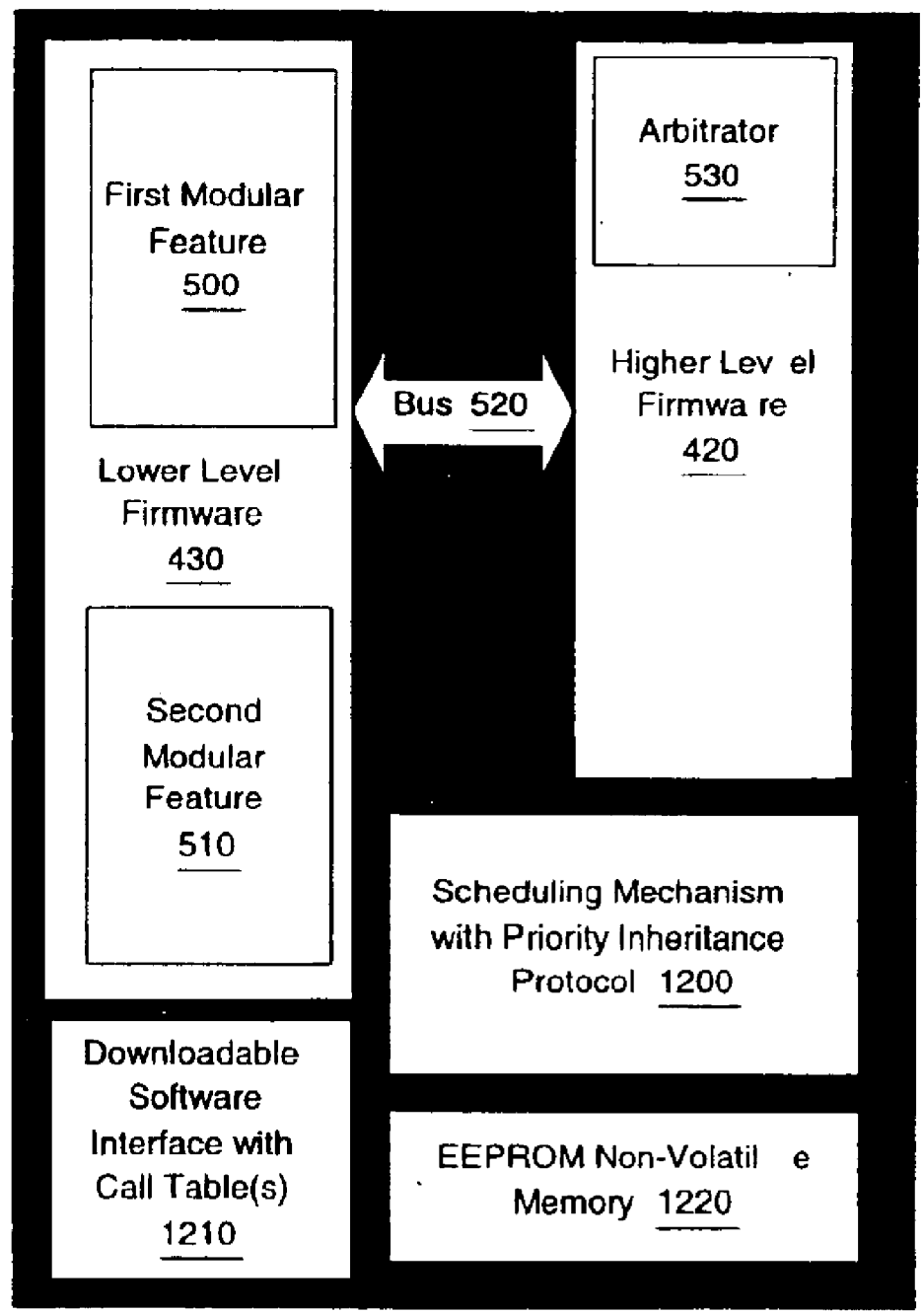

As shown in FIG. 12, the implantable medical device (IMD) controller 410 with the pre-emptive real-time operating system (RTOS) may have a scheduling mechanism 1200 with a priority inheritance protocol. The implantable medical device (IMD) controller 410 with the pre-emptive real-time operating system (RTOS) having the scheduling mechanism 1200 with the priority inheritance protocol may be capable of being analyzed using rate monotonic analysis. The implantable medical device (IMD) controller 410 with the pre-emptive real-time operating system (RTOS) having the scheduling mechanism 1200 with the priority inheritance protocol may be used in devices and/or systems that are resource-constrained, in terms of read-only memory (ROM), random access memory (RAM), power consumption, central processing unit (CPU) bandwidth, and the like. The implantable medical device (IMD) controller 410 with the pre-emptive real-time operating system (RTOS) having the scheduling mechanism 1200 with the priority inheritance protocol may also have a downloadable software interface 1210 with one or more call tables and/or an electrically erasable programmable read-only memory (EEPROM) non-volatile memory 1220.

The firmware architecture of the implantable medical device (IMD) controller 410 is designed to be modular and/or extensible and provides improved support for downloadable software, also known a RAMware. In various illustrative embodiments, the firmware architectural improvements include the use of a real-time operating system (RTOS) that provides pre-emptive scheduling and has facilities to prevent deadlock and unbounded priority inversion as well as support for rigorous timing analysis.

Downloadable software (RAMware) is the ability to load new software (executable code and not merely parameter values) into the implantable medical device (IMD) controller 410 via telemetry, for example, through a downloadable software interface 1210 with one or more call tables, as described above. This downloadable code (RAMware) may be backed up in an electrically erasable programmable read-only memory (EEPROM) non-volatile memory 1220, for example, so that the downloadable code (RAMware) could provide a permanent change to the therapy program for the implantable medical device (IMD) 400 that is capable of surviving a device reset.

The firmware architecture of the implantable medical device (IMD) controller 410, in various illustrative embodiments, uses pre-emption and allows downloadable software (RAMware) applications to create their own independent tasks. This is unlike conventional devices, as described above, in which the RAMware applications have to reside among the existing "tasks" in the embedded firmware, where the RAMware applications could create timing problems, making it difficult for the firmware to achieve all of the firmware deadlines.

The firmware architecture of the implantable medical device (IMD) controller 410, in various illustrative embodiments, makes use of event-driven intertask communication, call tables and a pre-emptive real-time operating system (RTOS). Consequently, the firmware architecture of the implantable medical device (IMD) controller 410, in these various illustrative embodiments, allows a downloadable software (RAMware) application to be designed in a similar manner to the design of a read-only memory (ROM)-resident application. The downloadable software (RAMware) applications in the implantable medical device (IMD) controller 410, in these various illustrative embodiments, have access to the full range of functionality provided in the embedded firmware, including all pre-emptive real-time operating system (RTOS) services. The downloadable software (RAMware) function calls may be inserted and/or appended to read-only memory (ROM)-resident function call tables. Alternatively, and/or additionally, the downloadable software (RAMware) function calls may replace read-only memory (ROM)-resident entities in the function call tables.

A downloadable software (RAMware) application in the implantable medical device (IMD) controller 410, in these various illustrative embodiments, may be created as a new foreground task. Similarly, since the downloadable software (RAMware) application in the implantable medical device (IMD) controller 410, in these various illustrative embodiments, may be backed up in an electrically erasable programmable read-only memory (EEPROM) non-volatile memory, the downloadable software (RAMware) application may be offered as a permanent, life-critical therapy without concern about being lost due to a device reset. Furthermore, a temporary downloadable software (RAMware) application, for research-oriented purposes, for example, may be downloaded "on top of" a permanent downloadable software (RAMware) application, allowing devices with permanent downloadable software (RAMware) applications to be included in research studies.

The downloadable software (RAMware) applications in the implantable medical device (IMD) controller 410, in various illustrative embodiments, may be thoroughly analyzed to allay concern for possible disruption of the proper functioning of read-only memory (ROM)-resident features, since the architecture may be subjected to rigorous timing analysis, due to inclusion of a priority inheritance protocol in the pre-emptive real-time operating system (RTOS).

The modular features may operate in the "rate domain," where calculations are performed in units of beats per minute (bpm). Using 8-bit values for these calculations can provide a resolution of 1 beat per minute (1 bpm) steps over a range from 0 bpm to 255 bpm ($2^8=256$), which is acceptable for brady and tachy therapy applications. In alternative illustrative embodiments, 16-bit values for calculations may be used that can provide a resolution of 1 operation per minute (1 oppm) steps over a range from 0 oppm to 65535 oppm ($2^{16}=65536$), which is acceptable for certain types of neurological therapy applications.

As described above, some modular features output a desired pacing rate, and a higher level firmware "arbitrator" (such as firmware arbitrator 530 disposed in the higher level firmware 420, as shown in FIG. 5) may decide to use the desired pacing rate output by the modular feature or use another value from a different modular feature. In the simplest form, the highest pacing rate is chosen by the higher level firmware arbitrator. In a more complex form, a higher pacing rate may lose priority to some modular feature that has a lower pacing rate. Some modular features output an offset value, and a higher level firmware operation may combine some or all of the offset values, for example, as in Atrial Ventricular (AV) adaptation. Some modular features may pass through one or more parameter values, either unmodified or modified, for example, as in a Sensing Atrial Ventricular (SAV) parameter value passing through an Auto Post-Ventricular Atrial Refractory algorithm.

During temporary operation, key pacing therapy parameters, such as Mode, Escape Interval, Pacing Atrial Ventricular (PAV) interval, Sensing Atrial Ventricular (SAV) interval, Post-Ventricular Atrial Refractory Period (PVARP), and the like, are held at static values and are not modified by modular features in the therapy flow. Consequently, modular features do not have to be disabled during temporary operations.

Each modular feature, such as the first modular feature 500 and the second modular feature 510, may be a firmware subroutine, for example, in the lower level firmware 430. Each modular feature firmware subroutine may be called by the higher level firmware 420. When each modular feature is called by the higher level firmware 420, the modular feature first checks to see if that particular modular feature is programmed to be "on," and then checks for mode pertinency. That particular modular feature algorithm continues to run if, and only if, all the checks pass (that particular modular feature is programmed to be "on" and is pertinent). Otherwise, that particular modular feature outputs a characteristic default value, such as the relevant rate or offset value, and/or an unmodified value, and ends.

Furthermore, in alternative embodiments of the present invention, a modification to the operation of the implantable medical device 400 can be performed. In particular, embodiments of the present invention provide for efficiently modifying the execution of firmware code residing in the implantable medical device 400. Embodiments of the present invention provide for a method and apparatus for patching, modifying, and/or updating firmware code and the functionality of the implantable medical device 400 in a remote fashion (i.e., communicating using a wireless format or other remote communication methods). In one embodiment, these modifications can be made in the field during operation of the implantable medical device 400.

In one embodiment, a hardware/firmware trap (firmware trap) is provided to interrupt the normal flow of execution of software code in the implantable medical device 400, and to execute additional trap/patch software code (e.g., additional code added to the implantable medical device 400 via the programming unit 120). In one embodiment, when the trap/patch software code (patch code) is executed, the execution flow of the original software code (firmware code) in the implantable medical device 400 is resumed. At least one advantage provided by implementation of the present invention is that the normal firmware execution by the implantable medical device 400 can be preempted temporarily, and then returned to the point in the firmware from which a branch was taken, with virtually minimal external code and effort.

Figure 13:
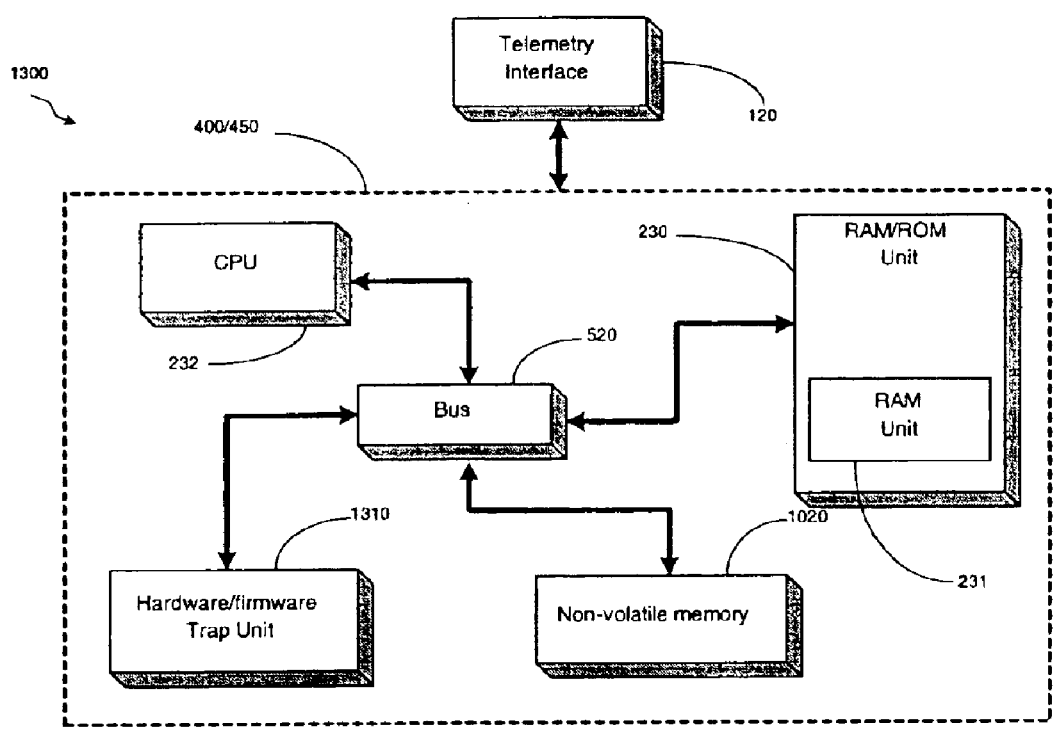

Turning now to FIG. 13, a block diagram depiction of one embodiment of implementing a hardware/firmware trap, in accordance with one embodiment of the present invention, is illustrated. In one embodiment, the CPU 232 performs tasks that are dictated by firmware stored within the implanted medical device 400. The firmware, which comprises programs for execution by the CPU 232, may be stored in the RAM/ROM unit 230. The CPU 232 acquires program data from the RAM/ROM unit 230 via the bus 520. In an alternative embodiment, the firmware code may be stored in a non-volatile memory 1020. In one embodiment, the non-volatile memory 1020 may comprise an EEPROM, a PROM, a flash memory unit, and/or other non-volatile memory devices.

In one embodiment, a hardware/firmware trapping system 1300 may be implemented such that during the execution of firmware code, the CPU 232 may be interrupted and an additional set of code (i.e., trap/patch code) may be executed at a different location, and subsequently, the operation of the implantable medical device 400 may then be brought back to the firmware code. In one embodiment, a set of software code (i.e., trap/patch code) may be transferred from the non-volatile memory 1020 and moved into a RAM unit 231 in the RAM/ROM unit 230 for an interrupt execution of the set of code. In one embodiment, the RAM unit 231 may comprise of a plurality of RAM-semiconductor chips. After the execution of the trap/patch code, the CPU 232 may then return to the normal execution flow of the firmware code. The interruption of the normal flow of the execution of the firmware code, carried out by the CPU 232, may be performed by a hardware/firmware trap unit 1310. In one embodiment, the hardware/firmware trap unit 1310 may communicate with the CPU 232 via the bus 520.

Figure 14:
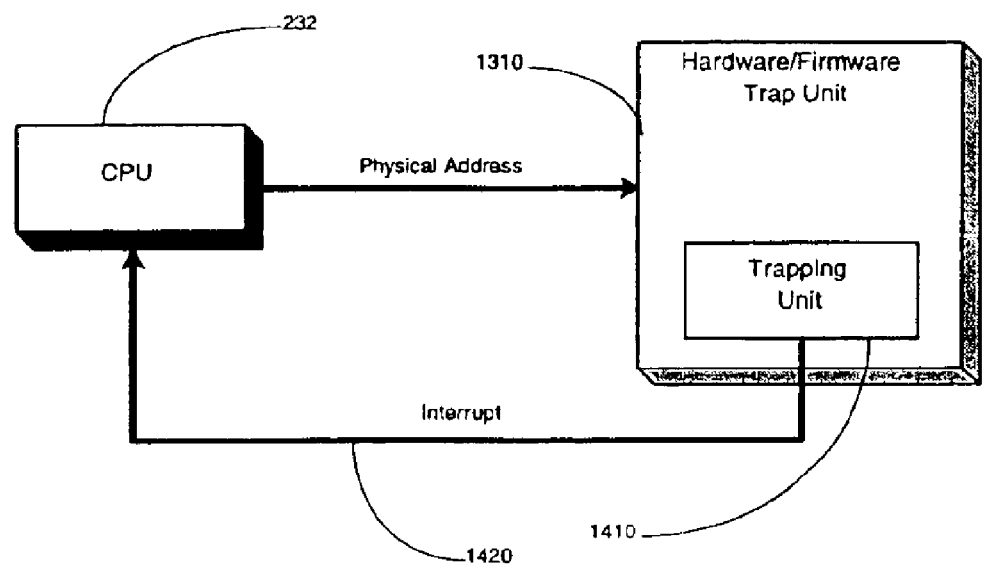

Turning now to FIG. 14, a block diagram depiction of an interaction between the CPU 232 and the hardware/firmware trap unit 1310, in accordance with one embodiment of the present invention, is illustrated. The CPU 232 may provide a physical address of the program code being executed, to the hardware/firmware trap unit 1310. Therefore, the hardware/firmware trap unit 1310 can monitor the execution flow of the firmware, as well as the operation flow of the implantable medical device 400, in order to determine an interrupt point for executing trap/patch software code.

The hardware/firmware trap unit 1310 may comprise a hardware unit, a software unit, a firmware unit, and/or a combination of the three. The hardware/firmware trap unit 1310 may monitor the physical address received from the CPU 232 and determines if an identifier, which identifies a particular physical address, has been received. In one embodiment, a trapping unit 1410 in the hardware/firmware trap unit 1310 checks the physical address received from the CPU 232 against a particular pointer that may be used to trap the firmware code being executed. In one embodiment, the trapping unit 1410 may assert an interrupt signal, which may be sent to the CPU 232, in response to the detection of a pointer or event where a hardware/firmware trap should be invoked into the firmware code. In one embodiment, the interrupt generated by the trapping unit 1410 may be a non-maskable interrupt (NMI), which interrupts the operation flow of the CPU 232.

The physical address received by the hardware/firmware trap unit 1310 may be one of a plurality of address-type such as an independent ROM address, a RAM address, memory-mapped register address, an address in the non-volatile memory 1020, and/or the like. Upon receiving the interrupt signal on a line 1420, the CPU 232 interrupts the normal flow of the execution of the firmware code and jumps to another location to execute the trap/patch code. Upon substantial completion of the trap/patch code, the CPU 232 then returns to the point of the jump, back to the normal flow of firmware execution.

Figure 15:
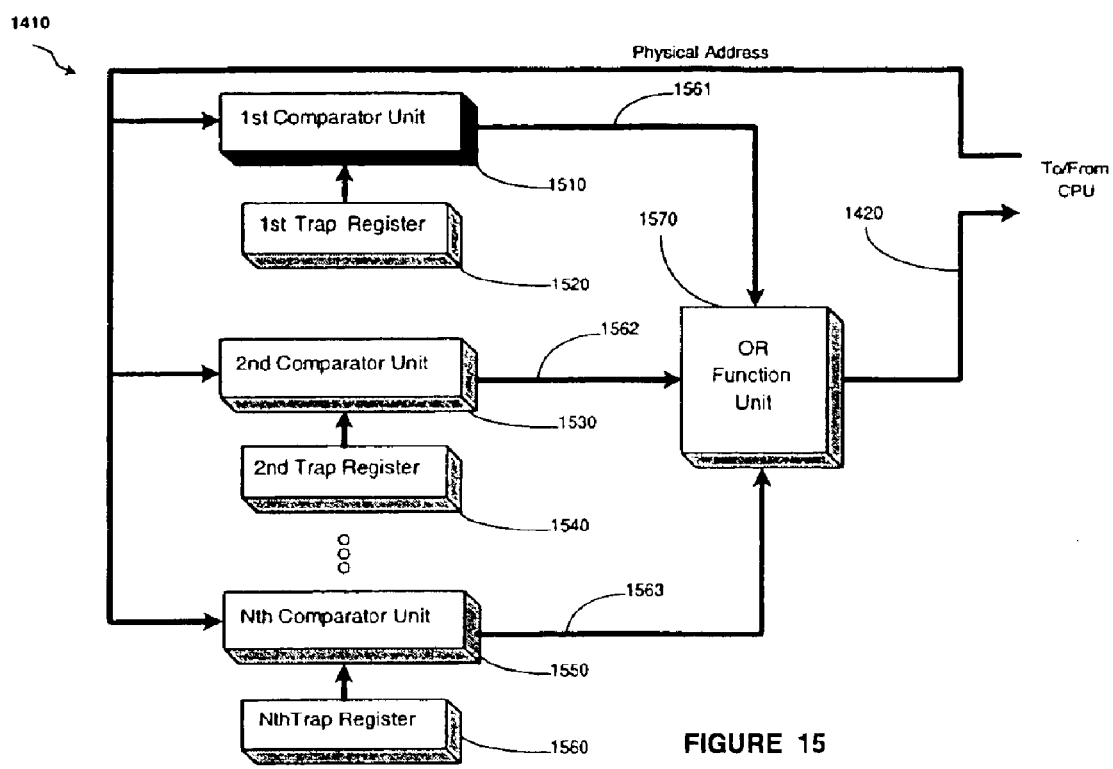

Turning now to FIG. 15, a block diagram depiction of one embodiment of the trapping unit 1410 in accordance with one embodiment of the present invention is illustrated. The trapping unit 1410 comprises a first comparator unit 1510, a second comparator unit 1530, to an Nth comparator unit 1550. In one embodiment, N is equal to 4, wherein the trapping unit 1410 may comprise four comparator units. However, it should be appreciated that any number of a plurality of comparator units may be present in the trapping unit 1410. In one embodiment, one or more comparator circuits may reside in each comparator unit 1510, 1530, 1550.

The trapping unit 1410 also comprises a first trap register 1520, a second trap register 1540, to an Nth trap register 1560, which respectively correspond to the first, second through Nth comparator units 1510, 1530, 1550. In one embodiment, each trap register 1520, 1540, 1560 provides a pointer address, which points to a set of trap/patch software code, to their corresponding comparator units 1510, 1530, 1550. The comparator units 1510, 1530, 1550 perform comparisons of the pointer addresses and the physical addresses, in order to determine whether a trap, or a hook, to interrupt the firmware execution flow, has been recognized. In other words, each of the comparator units 1510, 1530, 1550 compares a physical address to data stored in the corresponding trap register 1520, 1540, 1560, in order to determine whether a hardware/firmware trap condition has been met.

In one embodiment, the physical address may be a 16-bit address and the data in the trap register may also consist of a 16-bit value. The hardware/firmware trap unit 1310 may support the means for hardware to generate a NMI (Non-Maskable Interrupt) when an instruction is accessed at one of four independent ROM addresses, which may be a hardware/firmware trap. In other words, the hardware will "trap" the running firmware via the NMI. The addresses that get trapped may be determined by the value written into the trap registers 1520, 1540, 1560. In one embodiment, the register value written into the trap registers 1520, 1540, 1560 may comprise sixteen of the seventeen bits of the ROM physical address. Therefore, even and odd addresses may be considered the same and the normal 20-bit physical address, may be stripped of the ROM index.

To reduce the duplicity between even and odd addresses, a Load Instruction (LI) signal and a Chip Select (CS) may also be part of the comparative operation. In one embodiment, the NMI may be cleared by hardware/firmware trap unit 1310 performing a write to at least one of the trap registers 1520, 1540, 1560. In one embodiment, a write into the trap registers 1520, 1540, 1560 is performed, prior to the hardware/firmware trap unit 1310 enabling the NMI vector. This may reduce the possibility of the hardware/firmware trap being invoked into an unintended location. Furthermore, hardware/firmware traps may be disabled by loading a RESET value (e.g., 0xFFFF as the trap address into the trap registers 1520, 1540, 1560) into the trap registers 1520, 1540, 1560.

Any one of the sets of the comparator units 1510, 1530, 1550 and trap registers 1520, 1540, 1560 may assert a hardware/firmware trap detection signal on a line 1561, 1562, or 1563, which may be collected by an OR-function unit 1570, which may comprise one or more OR gates. The assertion of any one of the hardware/firmware trap detection signals on the lines 1561, 1562, or 1563 will prompt the OR-function unit 1570 to assert the interrupt signal on the line 1420. The interrupt signal on the line 1420 is then sent to the CPU 232 to interrupt the flow of the firmware execution in order to perform the instructions dictated by the trap/patch code. Upon completion of the patch code, which in one embodiment is run from the RAM unit 231, the program flow is returned to the position of the jump made from the firmware code.

In one embodiment, the instruction in the firmware execution flow upon which the hardware/firmware trap is triggered, is generally not executed. The NMI is triggered sufficiently fast enough such that the interrupt may be taken by the CPU 232 before the current instruction in the firmware is executed. Furthermore, the return address on a stack prior to a RTI may be modified. Therefore, the particular hardware/firmware trap may be prevented from being re-triggered. In order to execute the firmware instruction upon which a hardware/firmware was trapped, in one embodiment, that particular instruction in the firmware is executed within the time period of the interrupt service routine prompted by the NMI.

In one embodiment, the trap/patch software code is stored in the non-volatile memory 1020 and moved to the RAM unit 231 for execution. Generally, the firmware code is executed from a ROM space in the RAM/ROM unit 230, in contrast with the trap/patch code, which may be executed from the RAM unit 231. Accordingly, the total use of program execution from the RAM unit 231 is reduced, thereby increasing the stability of the overall implantable medical device 400. In an alternative embodiment, the trap/patch code may be executed from other memory devices such as the non-volatile memory 1020. It should be appreciated that the trapping unit 1410 may comprise other logic circuit/software/firmware, such that a number of methods can be used to assert the interrupt signal on the line 1420 based upon identifying a hardware/firmware trap situation. For example, the trap detection signals on the lines 1561–1563 can be asserted and an interrupt signal can be asserted on the line 1420, based upon a program counter used to locate a specific location in a firmware program flow, a specific event (e.g., end of a pacing therapy), or other conditions.

Figure 16:
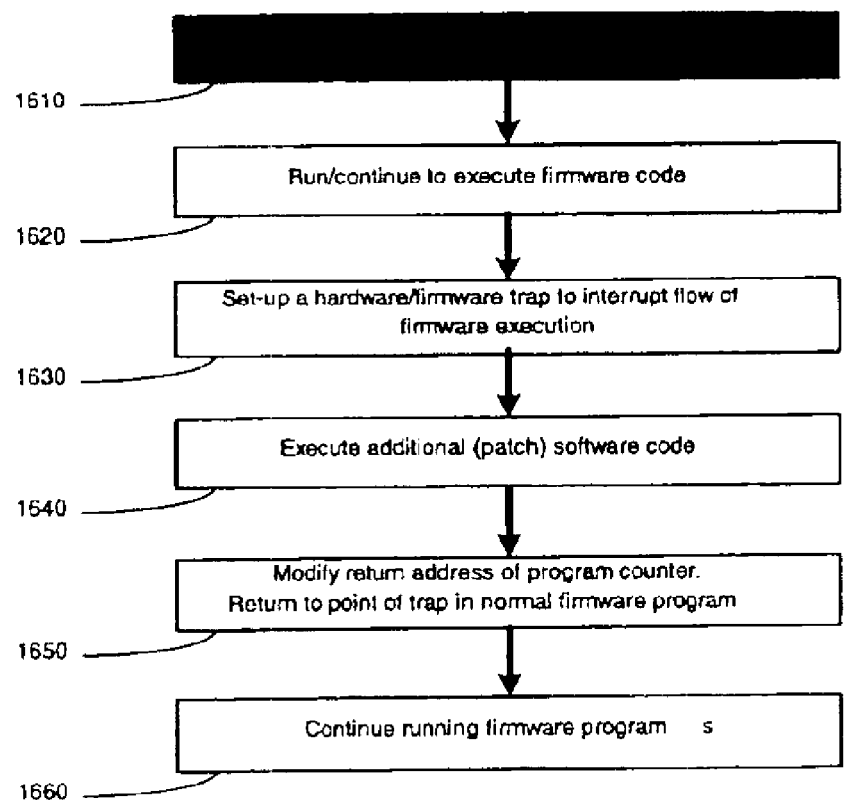

Turning now to FIG. 16, a flowchart depiction of the method of invoking a hardware/firmware trap, in accordance with one embodiment of the present invention, is illustrated. In one embodiment, a modification to be made to the normal execution of the firmware operation of the implantable medical device 400 is determined (block 1610). In one embodiment, a physician or operator can alter the operation of the implantable medical device 400 by invoking a change into the firmware code. For example, the voltage level of a cardiac therapy to be delivered may be modified. The change to the operation of the implantable medical device 400 may be created by modifying or adding a set of trap/patch software codes. Modifications, corrections, and/or upgrades to the operation of the implantable medical device 400 may be performed by adding the trap/patch software into the implantable medical device 400. More specifically, modifications, corrections, and/or upgrades to the operation of the implantable medical device 400 may be performed by executing the trap/patch software code at particular intervals within the execution flow of the firmware code.

The implantable medical device 400 performs its operations by running the firmware code (block 1620). In one embodiment, the firmware is continuously executed by the CPU 232. In order to apply the trap/patch software code to the operation of the implanted medical device 400, a hardware/firmware trap is set up in order to interrupt the firmware execution flow performed by the CPU 232 (block 1630). In one embodiment, a trap can be set up using a variety of techniques, such as program counters, checking for particular predetermined events, and/or other conditions.

Hardware/firmware traps may also be set up in a particular memory location such that any device in the implantable medical device 400 accessing a particular memory location is sent or jumped to a trap/patch software code. A program counter can maintain a numerical track of the flow of the execution of the firmware code, and enter into a jump situation based upon a particular program counter. Furthermore, events, such as the end of a pacing therapy delivery, can prompt the implantable medical device 400 to jump from a position of execution of the firmware, to the execution of the trap/patch software code.

Upon the interrupt of the firmware execution flow, the implantable medical device 400 may execute the additional trap/patch software program (block 1640). The execution of the additional trap/patch code may be utilized to correct problems with existing operations of the implantable medical device 400, to add a new function, and/or to upgrade the operation or software of the implantable medical device 400, and the like. A new function can be added to the implantable medical device 400 by executing the additional trap/patch software program. For example, new diagnostic data can be recorded based upon the execution of the additional trap/patch software code. Furthermore, a particular task can be added to the implantable medical device 400 based upon the execution of the additional trap/patch software code. For example, the implantable medical device 400 may perform a particular task every day at 3:00 a.m. In one embodiment, the trap/patch software code is generally executed in the RAM unit 231.

Once the additional trap/patch software code is executed, the implantable medical device 400 may return to normal execution of the firmware program (block 1650). In other words, upon completion of the trap/patch software code, the CPU 232 may return to the point of the execution order where the interrupt was received (i.e., the position of the firmware execution flow where the hardware/firmware trap was set). Furthermore, the return address of the program counter may be modified. Once the execution of the firmware code has returned to its normal position, the CPU 232 continues to execute the firmware code and the operation of the implantable medical device 400 continues in a normal fashion (block 1660).

Figure 17:
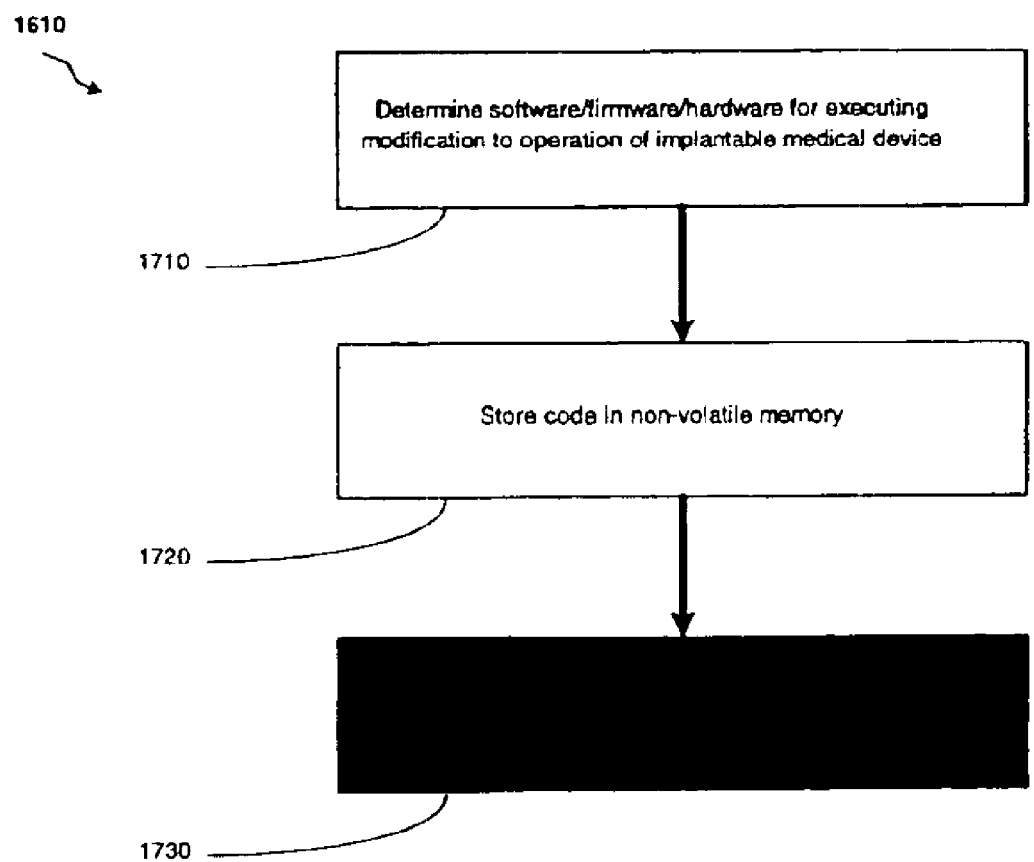

Turning now to FIG. 17, a flowchart depiction of one embodiment of determining/defining a modification to be made to the operation of the implantable medical device 400, in accordance with one embodiment of the present invention, is illustrated. The software, hardware, or firmware for executing the modification (i.e., the patch/modification/upgrade) to the operation of the implantable medical device 400 is determined (block 1710).

The trap/patch software code (patch code) is then stored in non-volatile memory 1020 in the implantable medical device 400 (block 1720). In one embodiment, trap/patch software code may be downloaded into the implantable medical device 400 via the programming unit 120. In an alternative embodiment, the trap/patch software code may be formed with the implantable medical device 400 based upon inputs received from the programming unit 120.

In one embodiment, the trap/patch code is stored in the non-volatile memory 1020, such as a PROM, an EEPROM, a flash memory, and/or the like. Furthermore, a pointer/address to enable the CPU 232 to locate and recognize a hardware/firmware trap is provided to the implantable medical device 400 (block 1730). Using the information provided by performing the steps indicated in FIG. 17, the hardware/firmware trap unit 1310 and the CPU 232 may be enabled to set up a hardware/firmware trap to interrupt the firmware execution flow and execute the appropriate trap/patch software code. The substantial completion of the steps described in FIG. 17 substantially completes the step of determining/defining a patch/modification/upgrade to the operation of the implantable medical device 400, as indicated in block 1610 of FIG. 16.

Figure 18:
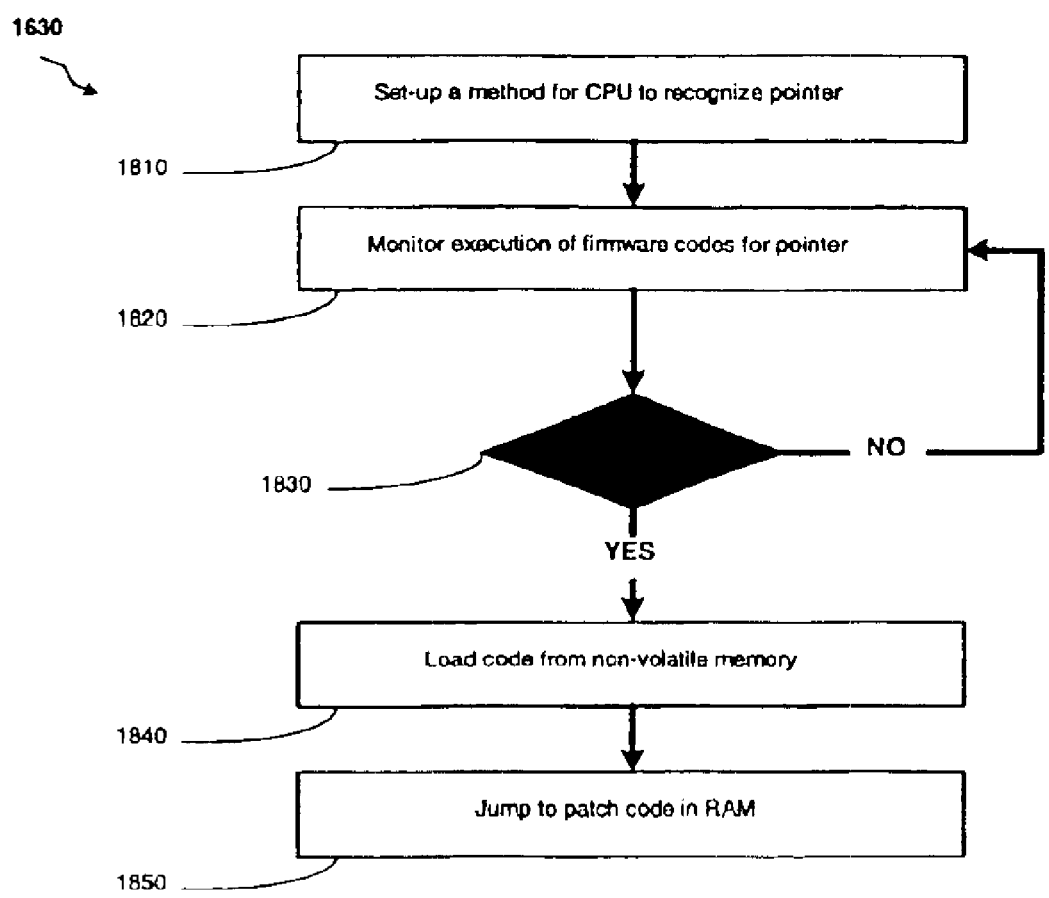

Turning now to FIG. 18, a flowchart depiction of one embodiment of performing the set up of a hardware/software trap in order to interrupt a firmware execution flow, described in block 1630 of FIG. 16, is illustrated. A method and/or means for the CPU 232 to recognize a pointer that leads to a trap/patch software code is set up and provided to the CPU 232 and the hardware/firmware trap unit 1310 (block 1810). In one embodiment, the trapping unit 1410 is provided to compare a physical address to a trap register address in order to determine if a hardware/firmware trap has been reached. The pointer/address that leads the CPU 232 to the trap/patch software may be a program counter used to count the number of executed program steps in the firmware, which may lead to a jump into the trap/patch software code. In an alternative embodiment, a particular event, such as an end of pacing therapy delivery, can trigger a jump to the trap/patch software code. Alternatively, the hardware/firmware trap can be set into a particular memory location, such that any access to that particular memory location will cause a jump to the trap/patch software code.

Once a means for the CPU 232 to recognize a pointer/address for a hardware/firmware trap is set up, the hardware/firmware trap unit 1310 monitors the execution of the firmware code to check for a particular pointer that may lead to a trap/patch software code (block 1820). When the hardware/firmware trap unit 1310 determines that a particular pointer has not been found, the trap unit 1310 continues to monitor the execution of the firmware code (block 1830).

When the hardware/firmware trap unit 1310 determines that a pointer is found, the hardware/firmware trap unit 1310 loads the trap/patch code from the non-volatile memory 1020, to the RAM unit 231 for execution (block 1840). Trap/patch software code generally moves from the non-volatile memory 1020 into the RAM unit 231 via the bus 520. In an alternative embodiment, the movement of the trap/patch software code may take place at an earlier period of time. The CPU 232, then jumps to the trap/patch code in the RAM unit 231 based upon the pointer/address (block 1850). At this point, the CPU 232 is enabled to execute a set of trap/patch software codes, which was found and presented by the hardware/firmware trap unit 1310. The completion of the steps described in FIG. 18 substantially completes the step of setting up a trap to interrupt the firmware program flow as indicated in block 1630. The implantable medical device 400 then continues with the execution of the steps described in FIG. 16. The teachings of the present invention may be applied to a variety of electronic devices and remain within the spirit of the present invention.

Any of the above-disclosed embodiments of a method and a device according to the present invention enables therapy features to be modular and/or extensible and resolves many feature-to-feature interactions in implantable medical devices. Additionally, any of the above-disclosed embodiments of a method and a device according to the present invention enables features to be easily and quickly added and/or modified and/or deleted in a given design and may create interim values for therapy features, simplifying the development and/or testing of those features. Furthermore, any of the above-disclosed embodiments of a method and a device according to the present invention enables features to operate in the "rate domain" in beats per minute (bpm), may make strategic conversions into the "interval domain" for parameter values that are loaded into hardware timing circuitry, may clearly identify where modular feature algorithms are working in the rate domain and/or in the interval domain and enables efficient use of conversion between the rate domain and the interval domain.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. In particular, every range of values (of the form, "from about a to about b," or, equivalently, "from approximately a to b," or, equivalently, "from approximately a–b") disclosed herein is to be understood as referring to the power set (the set of all subsets) of the respective range of values, in the sense of Georg Cantor. Accordingly, the protection sought herein is as set forth in the claims below.

What is claimed is:

1. A method, comprising:

controlling an implantable medical device using a controller using a pre-emptive real-time operating system (RTOS) having a scheduling mechanism, said controller having a firmware architecture;

executing at least one set of a firmware code for operation of said implantable medical device performing a modification to said operation of said implantable medical device, said modification to said operation comprising:

receiving a patch code;

creating a firmware trap;

generating an interrupt in response to said firmware trap; and executing said patch code in response to said interrupt.

2. The method of claim 1, wherein receiving a patch code further comprises storing said patch code in a non-volatile memory location with said device.

3. The method of claim 1, wherein creating a firmware trap further comprises monitoring said execution of said firmware to determine a match of a program counter.

4. The method of claim 1, wherein creating a firmware trap further comprises monitoring said execution of said firmware to check for a predetermined event.

5. The method of claim 1, wherein creating a firmware trap further comprises flagging a predetermined location in a memory location within said device.

6. The method of claim 1, wherein generating an interrupt in response to said firmware trap further comprises generating a non-maskable interrupt.

7. The method of claim 1, wherein generating an interrupt in response to said firmware trap further comprises moving said patch code from a non-volatile memory to a random access memory (RAM).

8. The method of claim 7, wherein executing said patch code further comprises executing said patch code stored in said random access memory (RAM).

* * * * *